(12) United States Patent
Marx et al.

(10) Patent No.: US 6,503,731 B2
(45) Date of Patent: *Jan. 7, 2003

(54) FIBRIN MICROBEADS PREPARED FROM FIBRINOGEN, THROMBIN AND FACTOR XIII FOR BINDING CELLS

(75) Inventors: Gerard Marx, New York, NY (US); Raphael Gorodetsky, Jerusalem (IL)

(73) Assignee: Hadasit Medical Research & Development Ltd., Jerusalem (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/153,547

(22) Filed: Sep. 15, 1998

(65) Prior Publication Data

US 2002/0006649 A1 Jan. 17, 2002

Related U.S. Application Data

(63) Continuation-in-part of application No. 08/934,283, filed on Sep. 19, 1997, now Pat. No. 6,150,505.

(51) Int. Cl.$^7$ ............................ C12P 21/06; C12N 5/06; C12N 7/02; C12N 11/02; A61K 35/14
(52) U.S. Cl. ...................... 435/69.1; 424/409; 424/489; 435/91.1; 435/177; 435/182; 435/239; 435/395; 435/403; 530/382; 530/383; 530/402
(58) Field of Search ............................... 435/174, 177, 435/182, 395, 397, 403, 69.1, 91.1, 239; 424/489, 529, 409; 530/382, 383, 402

(56) References Cited

U.S. PATENT DOCUMENTS

| | | | |
|---|---|---|---|
| 3,663,687 A | | 5/1972 | Evans .................. 424/1.25 |
| 3,937,668 A | | 2/1976 | Zolle .................. 424/1.29 |
| 4,147,767 A | | 4/1979 | Yapel, Jr. ................ 424/499 |
| 4,373,027 A | * | 2/1983 | Berneman et al. .......... 435/402 |
| 5,069,936 A | | 12/1991 | Yen .................. 427/213.33 |
| 5,260,420 A | * | 11/1993 | Burnouf-Fadosevich et al. ............ 530/382 |
| 5,324,647 A | * | 6/1994 | Rubens et al. .............. 435/180 |
| 5,411,885 A | * | 5/1995 | Marx ................. 435/402 |
| 5,635,609 A | * | 6/1997 | Levy et al. ............... 536/2 |
| 5,637,687 A | * | 6/1997 | Wiggins .................. 536/25.4 |
| 5,783,214 A | * | 7/1998 | Royer .................... 424/499 |
| 5,879,924 A | * | 3/1999 | Foster et al. ............. 435/235.1 |

FOREIGN PATENT DOCUMENTS

| | | | |
|---|---|---|---|
| JP | 05292899 | * | 11/1993 |
| WO | 9404261 | * | 8/1993 |
| WO | 9404260 | * | 3/1994 |

OTHER PUBLICATIONS

Lee, et al. Serum Albumin Beads: An Injectable, Biodegradable System for the Sustained Release of Drugs, *Science* 213:233–235 (1981).

Miyazaki, et al., Preparation and evaluation in Vitro and in Vivo of Fibrinogen Microspheres Containing Adriamycin, *Chem Pharm. Bull.* (Tokyo), 1986, 34(8): 3384–93.

Arshady, R., Microspheres and Microcapsules: A Survey of Manufacturing Techniques, Part I: Suspension Cross-Linking, *Polymer Engineering And Science* 29 (24): 1746–1758, 1989.

Arshady, R., Microspheres and Microcapsules: A Survey of Manufacturing Techniques. Part II: Coacervation, *Polymer Engineering And Science* 30 (15): 905–914, 1990.

Arshady, R., Microspheres and Microcapsules: A Survey of Manufacturing Techniques: Part III: Solvent Evaporation, *Polymer Engineering And Science*, 30 (15): 915–924, 1990.

Suslick, et al., Protein Microencapsulation of Non–Aqueous Liquids, *Journal of American Chemical Society* 112:7807–7809, 1990.

Yapel, Albumin Microspheres: Heat and Chemical Stabilization, *Methods in Enzymology* 112:3–43 (1985).

Ho et al. "Fibrin–based drug delivery systems. II. The preparation and characterization of microbeads," *Drug Develop. Industrial Pharm.* (1994) 20(4):535–546.*

Ho et al. "Fibrin–based delivery systems III: The evaluation of the release of macromolecules from microbeads," *J.Controlled Release* (1995) 34: 65–70.*

Miyazaki et al. "Fibrinogen microspheres as novel drug delivery systems for antitumor drugs," *Chem. Pharm. Bull.* (1986) 34(3): 1370–75.*

Dickinson et al. "Rheology of milk protein gels and protein–stabilized emulsion gels cross–linked with transglutaminase," *J. Agric. Good Chem.* (1996) 44: 1371–1377.*

Elisha Berman, et al., An Early Transient Increase of Intracellular Na+ may be one of the First Components of the Mitogenic Signal. Direct Detection by$^{23}$Na–NMR Spectroscopy in Quiescent 3T3 Mouse Fibroblasts Stimulated by Growth Factors. *Biochimica et Biophysica Acta* 1239, (1995), 177–185.

Richard I. Senderoff, et al., Fibrin Based Drug Delivery Systems. *Journal of Parenteral Science and Technology*, vol. 45, No. 1, Jan./Feb. 1991.

* cited by examiner

*Primary Examiner*—David M. Naff
(74) *Attorney, Agent, or Firm*—Amster, Rothstein & Ebenstein

(57) ABSTRACT

Fibrin microbeads are prepared containing extensively cross-linked fibrin (ogen) without using glutaraldehyde. The fibrin microbeads are preferably prepared by containing an aqueous solution containing fibrinogen, thrombin and Factor XIII with an oil heated to about 50–80° C. to form an emulsion and mixing the emulsion at 50–80° C. until fibrin microbeads containing extensively cross-linked fibrin (ogen) are obtained. The fibrin microbeads may have a diameter of about 50–200 microns and can contain a bioactive agent. The fibrin microbeads are used for binding cells such as when culturing or separating one cell type from another, or when transplanting cells or engineering tissue.

30 Claims, 15 Drawing Sheets

SEM of fibrin microbeads (FMB) with cultured cells.

FMB + Fibroblasts

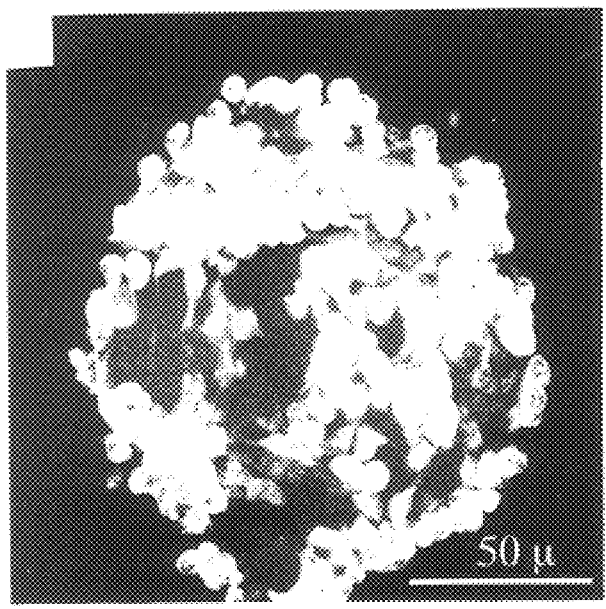
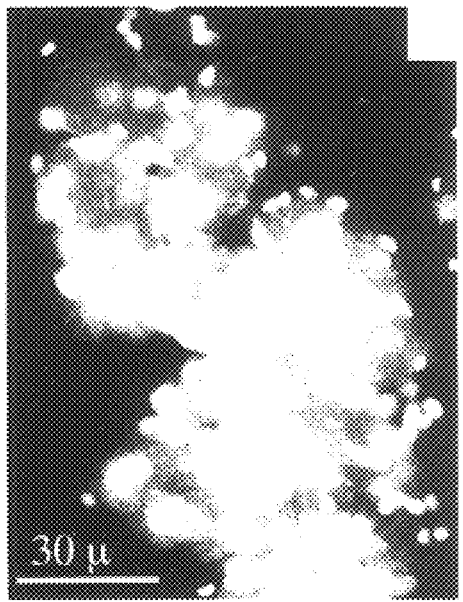
FIG. 8A
FIG. 8B
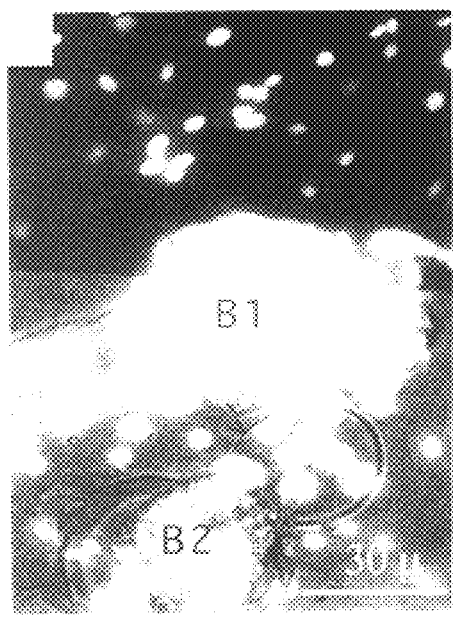
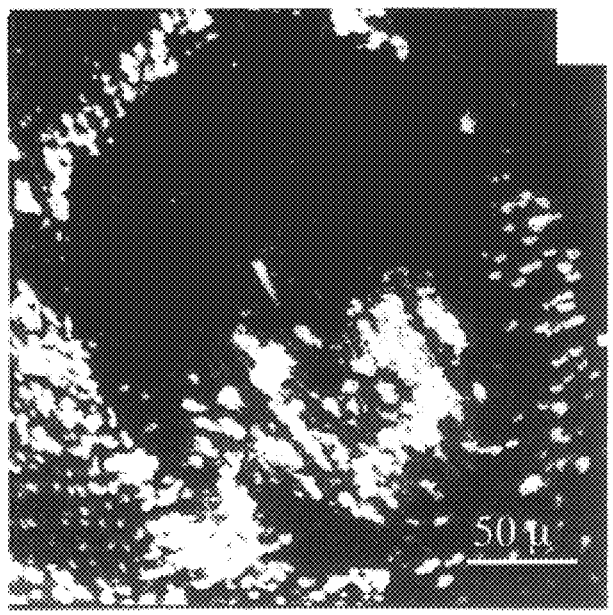
FIG. 8C
FIG. 8D

FIBRIN MICROBEADS PREPARED FROM FIBRINOGEN, THROMBIN AND FACTOR XIII FOR BINDING CELLS

This is a continuation-in-part of application No. 08/934,283, filed Sep. 19, 1997, now U.S. Pat. No. 6,150,505, the contents of which is hereby incorporated by reference in its entirety.

BACKGROUND OF THE INVENTION

The invention relates to fibrin microbeads, methods for preparing the fibrin microbeads, and their use as vehicles for culturing, separating and transporting cells, as vehicles for transplanting cells involved in wound healing, and as vehicles for tissue engineering.

Fibrin clots are formed in vivo based upon the reaction of fibrinogen and thrombin in the presence of calcium ions. The initial phase of wound healing starts after the formation of fibrin clot, and involves the mobilization of cells from surrounding undamaged tissue. Normally, the earliest cells mobilized to the wound are inflammatory where they are active for a period of at least 1–3 days following injury. Subsequently, they are displaced by cells of the mesenchyme lineage which are immobilized into, navigate through and digest fibrin and replace fibrin with extracellular matrix (ECM) of different collagen types, fibronectin and hyaloron. Endothelial cells also infiltrate the fibrin and generate microcapillary structures. Ultimately, these cells replace the provisional fibrin matrix with granulation tissue populated by parenchymal cells and vasculature in secreted ECM.

Human fibroblasts are the major cellular entities responsible for the regeneration of the extracellular matrix (ECM) within the wound bed. Human fibroblasts also express specific membrane receptors to fibrinogen and thrombin. In the case of skin wounds, human fibroblasts reform the matrix of the dermis. For example, during the course of healing of an incisional skin wound, human fibroblasts are mobilized from the surrounding tissue and enter into the fibrin clot, help dissolve it and generate as well as reform the collagens (i.e. type I and type III) in the extracellular matrix. Based upon these properties of human fibroblasts, fibroblast implants have been suggested as a means for supplementing the body's natural wound healing regime (Gorodetsky, R., et al. *Radiat. Res.* 125:181–186 (1991)).

Benzoylated hyaluronic acid (HA) sheets containing holes or pores have been used as a carrier for fibroblasts and keratinocytes for wound healing (Andreassi, L., et al. *Wounds* 3 (3): 116–126 (1991)). Specifically, HA sheets are cultured with these cells and then affixed to the site of the burn injury, where the cells migrate out of the sheet and accelerate the rate of wound re-granulation. A major problem with implanted HA sheets, however, is that they are not metabolized by tissue, are cumbersome to administer, and may result in long-term immunological problems.

Purified fibrin(ogen) (which is known in the art as a mixture of fibrin and fibrinogen) and several of its lytic fragments (i.e. FPA, FPB, D and E) have been shown to be chemotactic to a variety of cells including macrophages, human fibroblasts (HF) and endothelial cells (Gorodetsky, R., et al. *J. Lab. Clin. Med.*, in press (1997); Brown, L. F., et al. *Amer. J. Pathol.* 142:273–283 (1993); Clark, R. A. F., et al. *J. Invest. Dermatol.* 79:624–629 (1982); Ciano, P. S., et al. *Lab. Invest.* 54:62–69 (1986); Dejana, E., et al. *J. Clin. Invest.* 75:11–18 (1985)). Thrombin also has been shown to exert proliferative effect on various cells including fibroblasts, endothelial cells, and to enhance wound healing in rat skin (Kang, Y. H., et al. *J. Histochem. Cytochem.* 39:413–423 (1991); Shuman, F., *NY Acad. Sci.* 408:228–235 (1986); Biedermann, B., et al. *J. Lab. Clin. Med.* 124:339–347 (1994)).

Fibrin microbeads have been described in the prior art for use as drug delivery systems ((Ho, et al. *Drug Dev. and Ind. Pharm.* 20(4):535–546 (1994); Senderoff, et al. *J. Parenteral Sci. & Tech.* 45(1):2–6 (1991)). However, it has not been suggested or taught in the prior art that such fibrin microbeads have chemotactic and/or proliferative effects on any cells. Furthermore, the fibrin microbeads of Ho, et al. and Senderoff, et al. would not be particularly useful or desirable as vehicles for culturing cells. In this regard, the Ho, et al. microbeads contain glutaraldehyde which cross-links proteins and destroys certain biologically active sites, thereby interfering with the binding of the microbeads to cells. Glutaraldehyde treatment may also render the microbeads immunogenic. The Senderoff, et al. microbeads contain essentially the same relatively low degree of cross-linking as fibrin. Thus, the Senderoff, et al. microbeads are not stable in aqueous solutions and therefore would not be useful as vehicles for culturing cells which require matrices that do not readily dissolve in aqueous solutions.

SUMMARY OF THE INVENTION

The present invention provides fibrin microbeads that, unlike the fibrin microbeads of the prior art, do not contain any exogenous cross-linking agents such as glutaraldehyde that can damage certain biologically active sites that permit the microbeads to react with various types of cells. In addition, the fibrin microbeads of the present invention, unlike the prior art fibrin microbeads, contain extensive cross-linking of fibrin(ogen) which renders the fibrin microbeads stable for prolonged periods in aqueous solution, a property which is particularly desirable for use as vehicles for culturing cells, and for other uses.

Accordingly, it is an object of the present invention to provide fibrin microbeads that are biologically active and comprise extensively cross-linked fibrin(ogen).

It also is an object of the present invention to provide a method for preparing the fibrin microbeads of the present invention.

It is a further object of the present invention to provide a composition comprising cells bound to the fibrin microbeads of the present invention.

It is a still further object of the present invention to provide methods for culturing and separating one cell type from another using the fibrin microbeads of the present invention.

In addition, it is an object of the present invention to provide a method for transplanting cells using the fibrin microbeads of the present invention.

It also is an object of the present invention to provide a method for promoting healing of a wound using cells bound to the fibrin microbeads of the present invention.

Finally, it is an object of the present invention to provide a method for engineering tissue using the fibrin microbeads of the present invention.

Additional objects of the present invention will be apparent from the description which follows.

BRIEF DESCRIPTION OF THE FIGURES

FIG. 5A shows the FMB and fibroblasts in culture, while FIG. 6A shows fibroblasts leaving FMB after being transferred to a new culture flask.

FIG. 7A represents the rates of attachment (haptotaxis) to fibroblasts, smooth muscle and endothelial cells. The % of the FMB that were attached to the cultured cells at different time points was monitored by light microscopy. FIG. 7B sets forth the rates of proliferation of pig kidney epithelial cells. About 1 million cells were loaded on FMB and maintained at different media conditions. Cell number on FMB was evaluated by the MTS assay.

FIGS. 8A–8D set forth micrographs of fibroblasts on FMB. FIG. 8A shows a confocal microscopy image of EMT-6 cells on a single FMB. The composite image of superimposed 50 optical slices reveals approximately 200 cells loaded on a single FMB. FIG. 8B shows fluorescent micrographs of HF, red PI stained nuclei, grown on small FMB. The high cell density aggregated the beads to form a tissue-like structure. FIG. 8C shows a combined fluorescent and light microscopy image of cells loaded on FMB and embedded in low density fibrin droplet on a tissue plate. The upper part is a fluorescence image of the PI red-stained nuclei. The lower half of the image is combined fluorescent with light microscopy that shows the borders of the fibrin gel and the cells migrating from the FMB (B1) and (B2) with the translucent outlines around B2 that indicate the gel digestion track. FIG. 8D shows composite superimposed slices taken by confocal microscopy of densely populated FMB as described in panel (c). The high intensity PI fluorescence of the nuclei show the position of cells digesting their way from the FMB and the surrounding fibrin.

FIG. 10A represents a wound with no addition other than human fibrin. No evidence of granulation tissue is shown.

FIG. 10B represents a wound containing exogenous PDGF-BB. Increased fibroblast number is shown beneath the wound, but no granulation tissue.

FIG. 10C represents a wound to which fibroblasts suspended in fibrin were added. Individual fibroblasts in the fibrin clot are evident, but granulation tissue is not shown.

FIG. 10D represents a wound to which fibroblasts suspended in a fibrin+PDFG-BB were added. Nascent granulation tissue is shown on the bottom of the wound (arrows) as well as increased numbers of individual fibroblasts in the fibrin clot.

FIG. 1E represents a wound to which FMB suspended in fibrin were added. FMB are shown along the base of the wound.

FIG. 10F represents a wound to which FMB suspended in fibrin+PDGF-BB were added. FMB are shown along the base of the wound and a great number of fibroblasts in the underlying subcutaneous tissue (arrows).

FIG. 10G represents a wound to which fibroblast loaded FMB suspended in fibrin were added. FMB are shown along the base of the wound. A large number of fibroblasts were observed between the FMB and the underlying subcutaneous tissue.

FIG. 10H shows a wound to which fibroblasts loaded FMB suspended in fibrin and PDGF-BB were added. FMB are shown along the base of the wound, and robust granulation tissue between the FMB and in the underlying subcutaneous tissue.

DETAILED DESCRIPTION OF THE INVENTION

Figure 1:
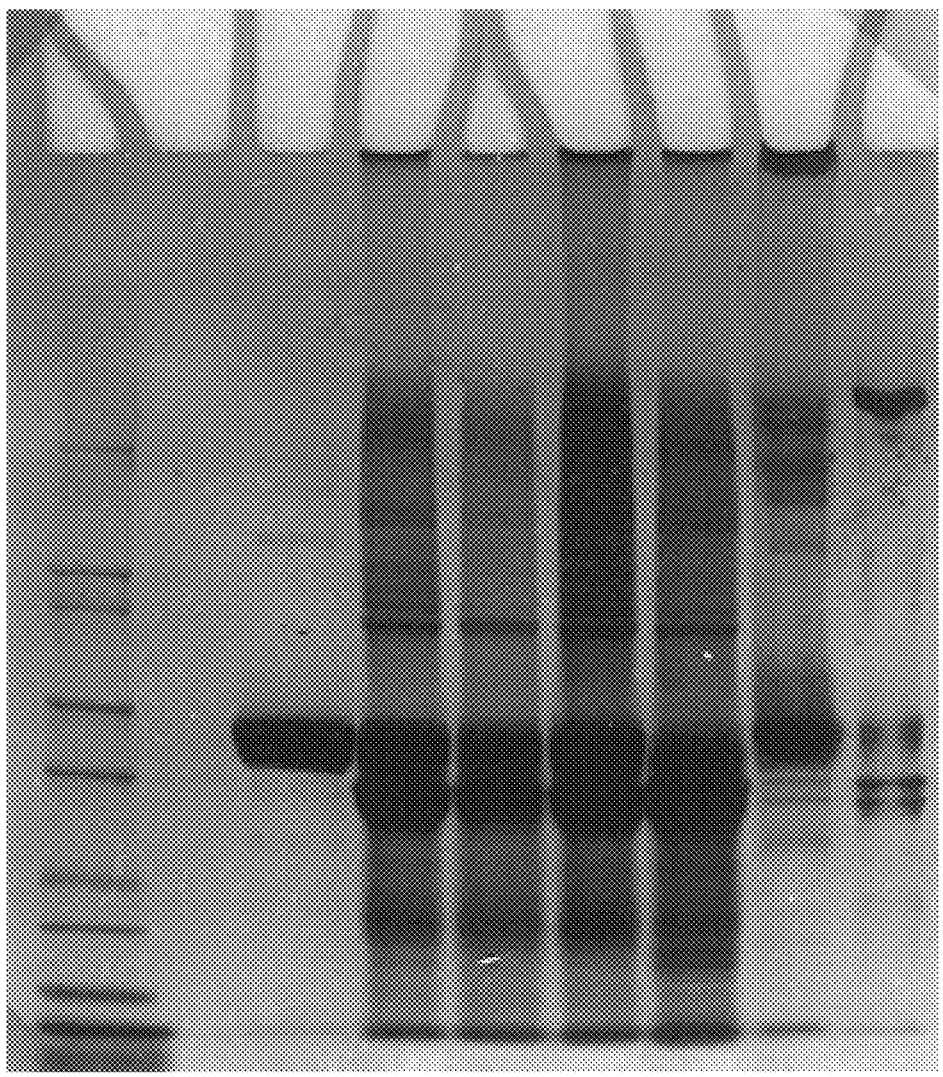
FIG. 1 represents an SDS-PAGE (non-reduced) of various FMB preparations of the present invention (lanes 3–7) in comparison with albumin (lane 2) and fibrin (lane 8). Lane 0 represents molecular weight (MW) marker, while lane 1 is blank. The results show that the fibrin microbead ("FMB") preparations of the present invention (lanes 3–7) are more extensively cross-linked than fibrin (lane 8).

The present invention is directed to biologically active, fibrin microbeads comprising extensively cross-linked fibrin (ogen). As used herein, "biologically active" means that the fibrin microbeads possess biologically active sites that permit the microbeads to attract and facilitate the growth of various types of cells. This is different than fibrin microbeads of the prior art that are treated with exogenous cross-linking agents, such as glutaraldehyde, which render fibrin microbeads unattractive to cells and biologically inactive.

"Extensively cross-linked" means that the fibrin(ogen) contains at least 30% cross-linked fibrin(ogen), and more preferably at least 50% cross-linked fibrin(ogen). The extensive cross-linking of the fibrin microbeads of the present invention is believed to occur during their manufacture, which utilizes high temperatures that help denature the native fibrin(ogen) structure, specifically the D-domain, thereby exposing sites for cross-linking by factor XIII, which are not normally cross-linked by native conformers of fibrin(ogen) at ambient temperatures. The SDS-PAGE gel patterns (FIG. 1) show extensive cross-linking due to such factor XIII mediated reactions. The extensive cross-linking renders the microbeads of the present invention insoluble and stable in an aqueous environment, thus rendering the microbeads stable for cell culturing and other uses.

It also is within the confines of the present invention that the fibrin microbead also may comprise at least one bioactive agent. Suitable bioactive agents include but are not limited to drugs, neurologics, vitamins, vitamin derivatives, growth factors, glucocorticosteroids, steroids, antibiotics, antibacterial compounds including bacteriocidal and bacteriostatic compounds, antiviral compounds, antifungal compounds, antiparasitic compounds, tumoricidal compounds, tumoristatic compounds, toxins, enzymes, enzyme inhibitors proteins, peptides, minerals, neurotransmitters, lipoproteins, glycoproteins, immunomodulators, immunoglobulins and fragments thereof, dyes, radiolabels, radiopaque compounds, fluorescent compounds, fatty acid derivatives, polysaccharides, cell receptor binding molecules, anti-inflammatories, antiglaucomic compounds, mydriatic compounds, anesthetics, nucleic acids, polynucleotides, and the like.

The fibrin microbeads of the present invention are produced in the following manner. First, an aqueous solution comprising fibrinogen, thrombin and factor XIII is prepared. This solution may be prepared by combining fibrinogen containing endogenous factor XIII with thrombin, by combining cryoprecipitate containing endogenous fibrinogen and endogenous factor XIII with thrombin, or by combining fibrinogen, factor XIII and thrombin individually into an aqueous solution. It also is within the confines of the present invention that equivalent proteases such as snake venom proteases (e.g. reptilase) may be used as an alternative to thrombin. The ratio of fibrinogen:thrombin:factor XIII in the aqueous solution is preferably 5–100 mg/mL:1–100 U/mL:1–50 U/mL, and most preferably 20–40 mg/mL:5–10 U/mL:2–20 U/mL. In addition to these proteins, the aqueous solution also may contain fibronectin and other blood-derived proteins that may be present in the fibrinogen and cryoprecipitate starting materials. If it is desired for the fibrin microbead to contain any bioactive agents, then those agents can be added into the fibrinogen or thrombin solutions prior to their mixing, or directly to the aqueous solution.

Next, prior to the onset of coagulation, the aqueous solution is introduced into an oil heated to a temperature in the range of about 50–80° C. to form an emulsion. A hydrophobic organic solvent such as isooctane also may be included in the oil. The inventors have found that using the concentrations of fibrinogen and thrombin presented in the Experimental Details Section below, coagulation occurs at about 30 seconds after the fibrinogen and thrombin are combined. However, for other concentrations of fibrinogen and thrombin, the onset of coagulation can be determined by using known coagulation assays.

Suitable oils include but are not limited to vegetable oils (such as corn oil, olive oil, soy oil, and coconut oil), petroleum based oils, silicone oils, and combinations thereof. Vegetable oils are preferred because they can be metabolized by cells and may provide nutrients to the cells. In the most preferred embodiment, the oil is corn oil. The inventors believe that minerals oils should be avoided since they are not metabolized by cells. In addition, oils that contain unsaturated bonds (i.e. Canola oil) should be avoided since they may be oxidized.

After the aqueous solution is introduced into the heated oil, the emulsion is then maintained at a temperature of about 50–80° C. and mixed at an appropriate speed until fibrin microbeads comprising extensively cross-linked fibrin (ogen) are obtained in the emulsion. The mixing speed will depend upon the volume of the emulsion, and the desired size of the microbeads. For volumes of 400 mL oil and 100 mL aqueous phase in a 1 L flask, the preferred mixing speed is 300–500 rpm. The emulsion is generally mixed for about 3–9 hours, although the actual time will vary depending upon the temperature, the concentration of the initial reactants and the volume of the emulsion. As discussed above, it is believed that at temperatures of about 50–80° C., the native fibrin(ogen) structure denatures exposing sites for cross-linking by factor XIII, which are not normally cross-linked at ambient temperatures. Such cross-linking occurs during the first phase of the mixing/heating cycle. The heating also serves the purpose of dehydrating the emulsified system (drying process) thereby producing cross-linked fibrin(ogen) particles that do not stick together or coalesce, as such particles do when they possess too much water.

Finally, the extensively cross-linked fibrin microbeads may be isolated from the emulsion using procedures such as centrifugation, filtration, or a combination thereof. The isolated fibrin microbeads may then preferably be washed with solvents such as hexane, acetone and/or ethanol, and then air dried. The microbeads may then be graded to the desired size using commercially available filters or sieves. Preferably, the fibrin microbeads of the present invention are graded to a diameter of about 50–200 microns, although larger or smaller fibrin microbeads may be sized, if desired.

The present invention also provides a composition comprising cells bound to the fibrin microbeads of the present invention. The cells include any cells that bind to the fibrin microbeads. Such cells include but are not limited to fibroblasts, endothelial cells, chondrocytes, neuroblastoma cells, kidney cells, liver cells, pancreatic cells, thyroid cells, glial cells, smooth muscle cells, mouse mammary carcinoma cells, bone/cartilage forming cells, and combinations thereof.

As certain cells also proliferate on the fibrin microbeads, the present invention also provides a method for culturing fibrin microbead binding cells with the fibrin microbeads of the present invention in a culture medium under conditions permitting the cells to bind to the fibrin microbeads. The advantage of culturing cells with the fibrin microbeads of the present invention is that the cells bind and grow on the fibrin microbeads. Thus, as the cells are needed for other uses, they may be easily removed from the cell culture medium by pipetting or pouring off the fibrin microbeads without trauma to the cells. This is a substantial improvement over conventional means for removing cells from culture plates such as trypsinization, which may damage certain receptors on the cells and otherwise cause trauma to the cells. The ability to transfer cells from one environment to another using the fibrin microbeads of the present invention also means that such cells can be reseeded into fresh culture medium with minimal damage to the cells.

In addition to these advantages, the fibrin microbeads of the present invention, because they attract and grow a population of cells that is significantly more dense than conventional cell cultures, can be used as a more efficient means for producing recombinant proteins, viruses, bacteria, the cloning of desirable nucleic acids, and the like, than conventional cell cultures. As such, it is envisioned that the cells cultured in connection with the fibrin microbeads of the present invention can be transformed or transfected with various vectors, viruses, bacteria, nucleic acid, and the like. In this manner, the fibrin microbeads of the present invention can be used as vehicles for the production of viruses, recombinant proteins, cloning of nucleic acids, and the like.

In addition, because not all cells bind to the fibrin microbeads of the present invention, the fibrin microbeads also are very useful for separating cells. In this regard, the present invention also provides a method for separating cells that bind to fibrin microbeads from a cell culture containing the fibrin microbead binding cells and cells that do not bind to fibrin microbeads. In this method, cells can be cultured with the fibrin microbeads in a growth medium under conditions permitting the fibrin microbead binding cells to bind to the fibrin microbeads. The cells of interest that bind to the microbeads can then be isolated from the culture medium by removing the fibrin microbeads.

Furthermore, because the fibrin microbeads of the present invention bind certain cells it also is envisioned that the microbeads can be used as a vehicle for transplanting such cells. For example, because the fibrin microbeads of the present invention bind cells involved in wound healing, the fibrin microbeads can be used to transplant wound healing promoting cells into a wound. As used herein, "wound" includes surgical wounds, burns, ulcers, lacerations, and the like. This can be accomplished by culturing the desired cells with the fibrin microbeads, and applying a wound healing effective amount of the cells bound to the fibrin microbeads to the wound. Suitable wound healing promoting cells include but are not limited to fibroblasts, smooth muscle cells, endothelial cells, chondrocytes, bone/cartilage forming cells and combinations thereof. It also is within the confines of the present invention that the fibrin microbeads may further comprise at least one bioactive agent selected from the group consisting of wound healing promoting agents, growth factors, glucocorticosteroids, steroids, antibiotics, antibacterial compounds, antiviral compounds, and antifungal compounds. The composition may be affixed to the wound using fibrin glue.

In addition, it also is envisioned that the fibrin microbeads may be used for transplanting cells that have been modified by known recombinant methods to express desirable proteins for treating diseases associated with a deficiency of these proteins. For example, vectors containing nucleic acid encoding insulin may be used to incorporate the nucleic acid into the cells by known recombinant techniques so that the cells express insulin. The insulin producing cells can then be cultured with the fibrin microbeads of the present invention and then introduced into the patient for treating diabetes. Other diseases that may be treated include but are not limited to hemophilia A (factor VIII deficiency) hemophilia B (factor IX deficiency) and cystic fibrosis.

Finally, because the fibrin microbeads of the present invention also bind cells involved in the formation of tissue, it is envisioned that the fibrin microbeads can also be used as a vehicle for facilitating tissue engineering. In this connection, a suspension of the desired cells can be prepared by culturing the cells with the fibrin microbeads. The suspension of the fibrin microbeads carrying the desired cells can then be applied to a surface of a prosthetic device using fibrin glue, for example, and the cells cultured in a tissue culture medium until the desired extracellular matrix or tissue is formed on the surface of the prosthetic device. The choice of cells will depend upon the tissue desired and include but are not limited to fibroblasts, endothelial cells, chondrocytes, neuroblastoma cells, kidney cells, liver cells, pancreatic cells, thyroid cells, glial cells, smooth muscle cells, bone/cartilage forming cells, and any combination thereof.

The present invention is described in the following Experimental Details Section which is set forth to aid in an understanding of the invention, and should not be construed to limit in any way the invention as defined in the claims which follow thereafter.

EXPERIMENTAL DETAILS SECTION
MATERIALS AND METHODS

Proteins.

The source of fibrinogen used in the experiments was either fibrinogen prepared by fractionation of pooled plasma, or cryoprecipitate obtained from frozen and thawed pooled plasma. The biochemical composition of the purified fibrinogen was as follows: 41±5 mg/mL protein, 40±5 mg/mL fibrinogen, 1±1 mg/mL fibronectin, trace IgG and 20±10 U/mL Factor XIII. The biochemical composition of the pooled cryoprecipitate was as follows: 72±10 mg/mL protein, 13±5 mg/mL fibrinogen, 3±1 mg/mL fibronectin, 13±2 mg/mL IgG and 5±1 U/mL Factor XIII. Thrombin was either bovine or human, and was prepared as described (Zou, et al. U.S. Pat. No. 5,677,162 (1997)) with unitage determined by clot time assays calibrated against an international standard.

FMB Preparation Protocol.

A typical preparation was carried out by heating 400 mL corn oil and isooctane to 55° C. with mechanical stirring. A solution of 25 mL fibrinogen (40 mg/mL) or cryoprecipitate (diluted 1:2 in Tris/saline buffer) was mixed with 5 mL thrombin to 5 U/mL (final concentration). This level induced coagulation within 30 seconds. After adding the thrombin but before coagulation occurred, the protein mixture was slowly added to the heated oil so that the stirring dispersed the aqueous phase into droplets suspended in the oil. Mixing and heating was continued for 1 hour. The isooctane evaporated out of the oil eventually, after which the temperature was elevated to approximately 75° C. Mixing continued for 4–8 hours. The heat was then turned off and stirring continued for 2 hours until the mixture reached room temperature.

The oil suspension was rendered less viscous by adding 100 mL hexane, filtered through a Whatman #42 filter paper, and the particulate FMB was rinsed with hexane. The crude FMB was then suspended in 50 mL 95% ethanol and homogenized for 1 minute. The FMB particles were allowed to settle for 10–20 seconds and the supernatant "fines" decanted. These procedures were repeated three times, after which the fibrin microbeads of the present invention ("FMB") were air dried, weighed and stored at 4° C. For sizing, the FMB were passed through a wire mesh to select for FMB of around 50–200 micron diameter.

Prior Art Fibrin Microbeads.

Fibrin microbeads were prepared essentially as described in Senderoff, et al., "Fibrin Based Drug Delivery Systems," *J. Parenteral Sci. & Tech.*, 45(1):2–6 (1991). Specifically, a fibrinogen solution was prepared from 50 mg of desalted, freeze-dried fibrinogen and 1.0 mL citrate buffer. The solution was then mixed with 2.5 units of thrombin, injected into 50 mL of heavy mineral oil, and then stirred at 1500 rpm. After a 30 minute incubation, the microparticles were separated and washed with ethyl acetate and 0.05% Tween 80. The microparticles were then dried over nitrogen gas to remove organic solvents.

Solubility Tests.

The FMB of the present invention were tested for solubility in Tris/saline or in 4 M urea monitored by phase contrast microscopy. Neither the Tris buffer nor the 4 M urea dissolved the FMB for up to 1 week at room temperature, though the latter did induce some swelling. As FMB are not soluble, they were partially digested to obtain material for analysis. 100 µg FMB were suspended in 1 mL 0.1 N NaOH, the supernatant samples were remover after 1 or 2 days and subjected to reduced 4–12% gradient SDS-PAGE (Nova, Encino, Calif.) using fibrinogen or normally clotted fibrin as controls.

SDS-PAGE.

Figure 2:
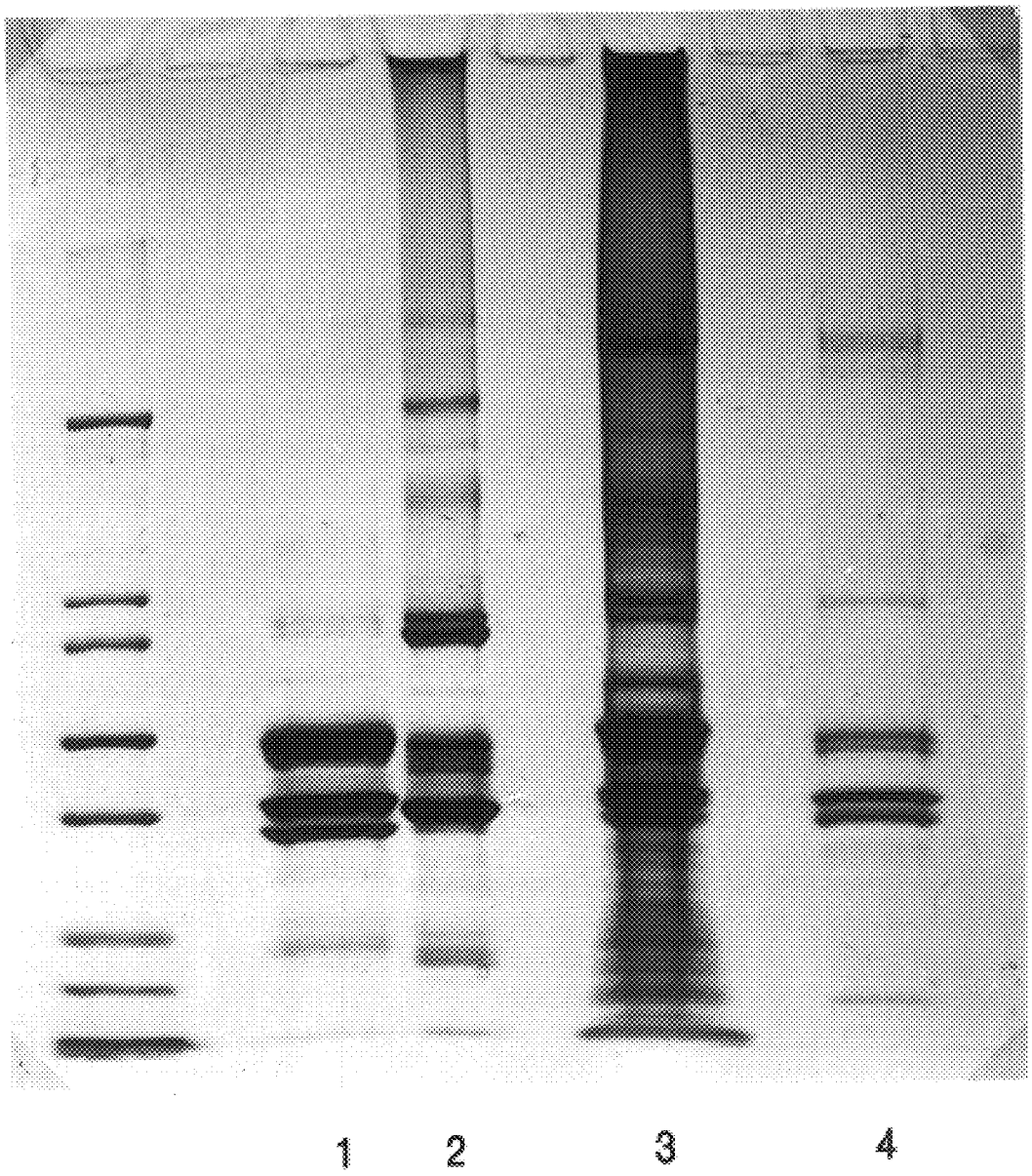
FIG. 2 represents an SDS-PAGE (reduced) of FMB preparation of the present invention (lane 3) in comparison with fibrinogen (lane 1), fibrin (lane 2) and microbead of Senderoff, et al. (1994) (lane 4). Lane 0 represents molecular weight (MW) marker. The SDS-PAGE shows that the FMB preparation (lane 3) of the present invention is significantly more cross-linked than fibrinogen (lane 1), fibrin (lane 2) and the microbead of Senderoff, et al. (1994) (lane 4).

Reduced SDS-PAGE of various FMB preparations of the present invention were carried out and compared to SDS-PAGE of albumin and fibrinogen. As shown in FIG. 1, the SDS-PAGE of FMB preparations of the present invention showed multiple cross-links far beyond that observed with fibrinogen. Similarly, SDS-PAGE was carried out for the FMB of the present invention and compared to SDS-PAGE of fibrinogen, fibrin and the microbead of Senderoff, et al. (1994). The results are presented in FIG. 2 and show that the FMB preparation of the present invention (lane 3) is significantly more cross-linked than fibrinogen (lane 1), normal clottable fibrin (lane 2) (which usually shows only γ—γ dimers, loss of α and γ bands and α—α multimers which do not enter the SDS-PAGE gel) and the microbead of Senderoff, et al. (1994) (lane 4).

Densitometric Tracings.

Figure 3A:
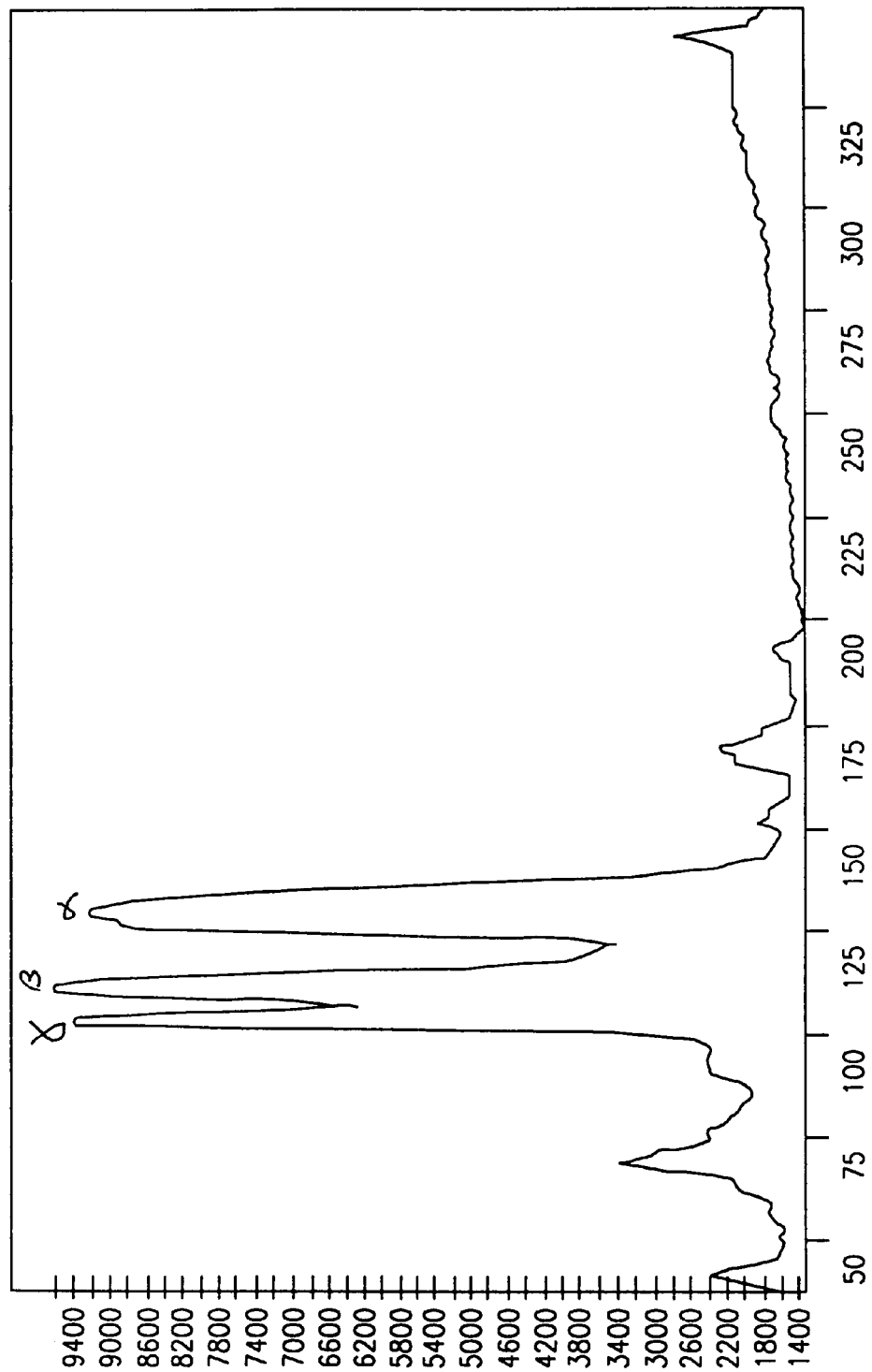
FIGS. 3A–3D represent densitometric tracings of fibrinogen (FIG. 3A), fibrin (FIG. 3B), the microbead of Senderoff, et al. (1994) (FIG. 3C) and the FMB preparation of the present invention (FIG. 3D). The densitometric tracings show that the FMB preparation of the present invention (FIG. 3D) is significantly more cross-linked than fibrinogen (FIG. 3A), fibrin (FIG. 3B) and the microbead of Senderoff, et al. (1994) (FIG. 3C).
Figure 3B:
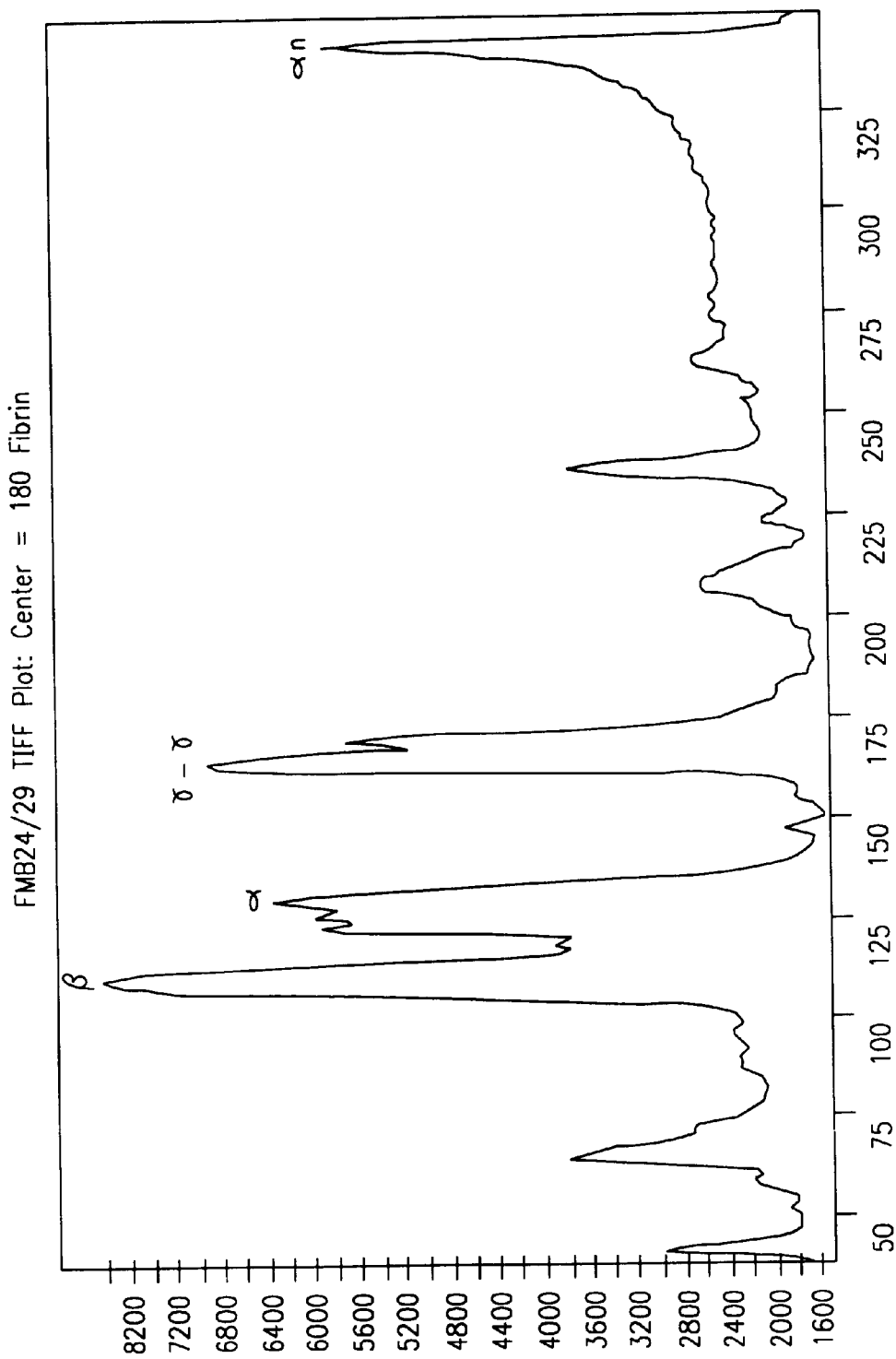
Figure 3C:
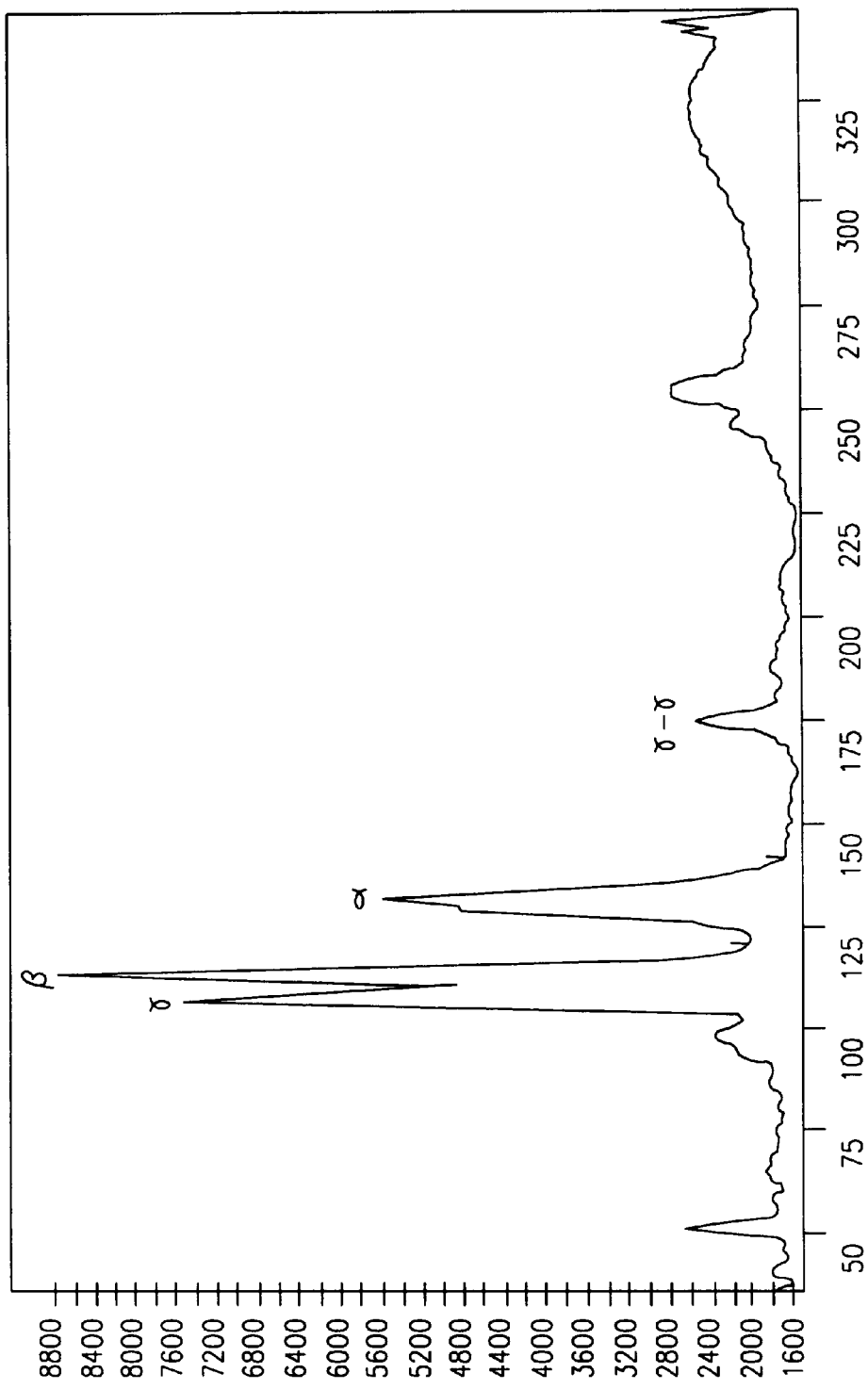
Figure 3D:
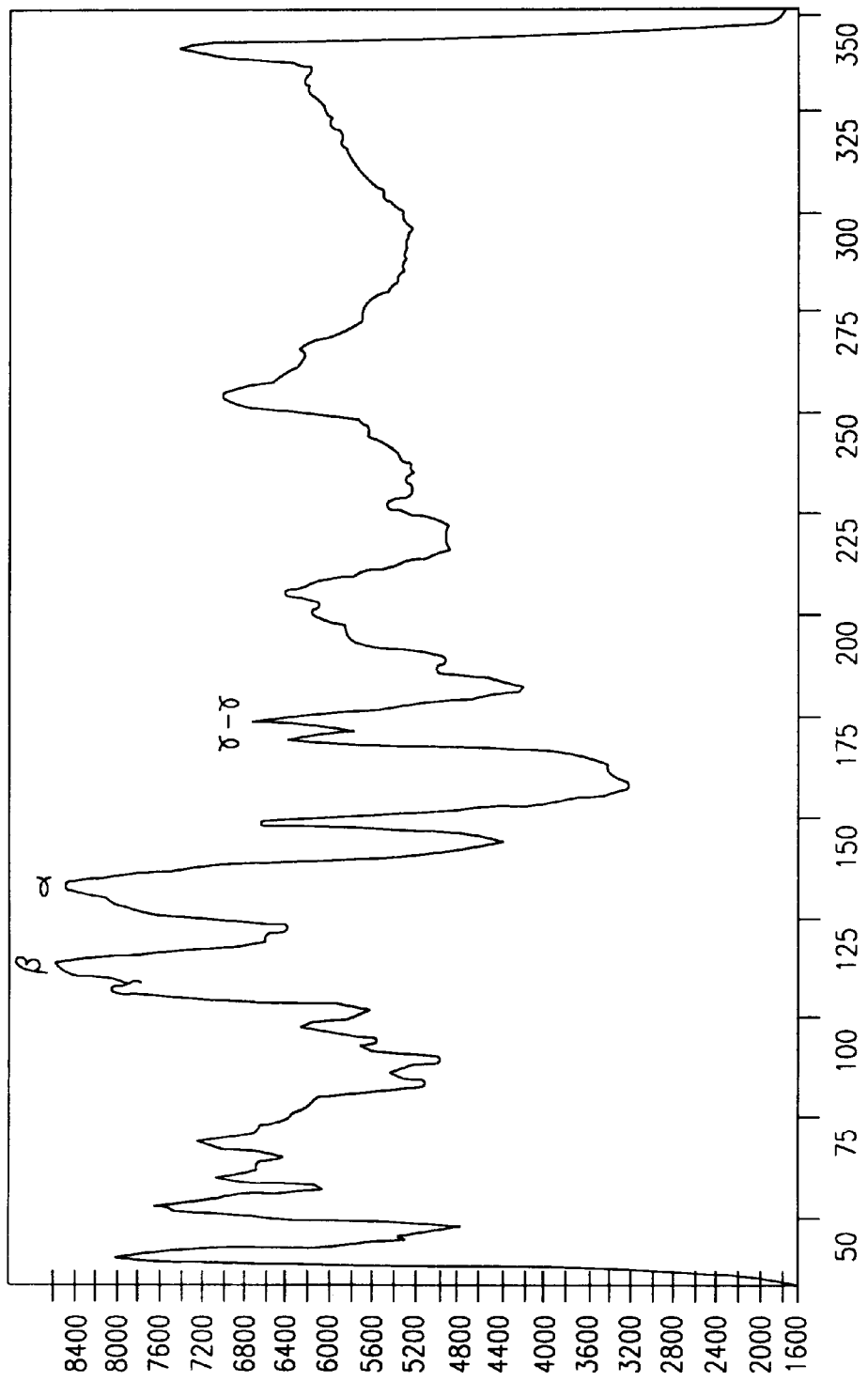

Densitometric tracings were prepared for fibrinogen, fibrin, the microbead of Senderoff, et al. (1994) and an FMB preparation of the present invention. Briefly, the SDS-PAGE (reduced) gel was scanned on a flat-bed scanner linked to a Mac-TCI-II computer. The optical density of the bands were digitalized and the resultant tracings are presented in FIGS. 3A–3D. As shown in the figures, the FMB preparation of the present invention (FIG. 3D) is significantly more cross-linked than fibrinogen (FIG. 3A), fibrin (FIG. 3B) and the microbead of Senderoff, et al. (1994) (FIG. 3C).

Cell Cultures.

Normal human fibroblasts (HF) were isolated from the foreskin of young human subjects who underwent voluntary circumcision. The dermal layer of skin was chopped and digested briefly by 0.25% trypsin/versen. The isolated cells were washed and plated on plastic Petri dishes with DMEM supplemented by 10% fetal calf serum (FCS), antibiotics, and glutamine. The plates were washed after 10 hrs to select for the better attached fibroblasts. After 3–4 passages, the cells microscopically consisted of a homogenous population of fibroblasts. Immunohistology with monoclonal anti-human-fibroblast surface proteins (Product F4771, Sigma, Rehovot, Israel) of cells isolated and grown in these conditions confirm that this procedure yields homogeneous fibroblast culture (Ronnov-Jessen, L., et al. *Histochem. Cytochem.* 40:475–486 (1992)).

Normal murine fibroblasts (MF) were isolated from the skin of 2–3 days old neonate C3H mice by 3 step digestion, each for 2 hrs, with trypsin/versen. The use of neonate mice with low cross linking of collagen enables the isolation of high yield of cells during the proteolytic digestion. The details of the rest of the protocol are similar to those used for the isolation and growth of HF. The cells were cultured similarly to the HF and the homogeneity of these cells following 3–5 passages was obvious microscopically. These cells could be grown for at least 12–14 passages before any slow-down in their rate of proliferation occurred. The cells from the 4th to the 10th passage were used.

Porcine smooth muscle cells (SMC) were isolated from thoracic aortas of young animals and kept in culture with twice medium change and splitting once in 1–2 weeks. Cells of up to 10 passages were used. The purity of the SMC culture was measured by immunohistology with monoclonal anti-muscle-specific-actin HHF-35 (Bar-Shavit, R., et al. *Cell Regul.* 1:453–463 (1990)).

Other cell lines were obtained from different sources and cultured in their standard conditions as described in the following references: murine fibroblast line (3T3) and normal human keratinocytes from Dr. H. Ben-Bassat (Ben-Bassat, H., et al. *Plastic & Reconstructive Surgery* 89:510–520 (1992)); murine mast cells (MC-9) from Dr. E. Razin (Razin, E. and G. Marx *J. Immunol.* 133:3282–3285 (1984)); normal bovine aortic endothelial cells (BAEC) from Dr. I. Vlodavsky (Vlodavsky, I., et al. *J. Cell Biol.* 83:468–486 (1979)); porcine smooth muscle from Dr. H. Shwalb, were isolated and cultured as previously described (Bar-Shavit, R., et al. *Cell Regul.* 1:453–463 (1990)); pig kidney epithelial cells from Dr. A. Lazo; murine leukemic cells (P-388) from Dr. A. Ramu (Ramu, A., et al. *Biochem. Pharmacol.* 42:1699–1704 (1992)); human ovarian carcinoma cells (OV-1063) were isolated by Dr. A. Horowitz (Horowitz, A. T., et al. *Oncology* 42:332–337 (1985)); murine mammary adenocarcinoma cells (EMT-6) were grown at their standard conditions (Rockwell, S. *Br. J. Cancer* 37:212–215 (1978)); murine macrophage-like cells (J774.2) were obtained from Dr. I. Ringel (Ringel, et al. *Cancer Res.* 45:3856–3863 (1985)); 4T1 murine mammary carcinoma cells were obtained from Dr. S. Morecki; and human melanoma cells were obtained from Dr. T. Peretz.

All culture medium ingredients were purchased from Biological Industries (Beit-HaEmek, Israel) and fetal calf serum was supplied by GIBCO (Grand Island, New York, N.Y., USA). The cell cultures were maintained at 37° C. in water-jacketed $CO_2$ incubators, and were harvested by trypsin/versen solution with 1–2 passages per week in a split ratio of 1:10 for fast proliferating transformed cells and 1:4 for normal cell types.

FMB Cell Culture Studies.

For FMB cell culture studies, $10^6$ cells were grown in 10% serum DMEM medium in a 50 mL culture flask to near confluence. The cells were trypsinized, harvested and counted. A 50 mL polycarbonate tube (punctured top) covered loosely with aluminum foil was then prepared. 0.5 mL of FMB (sterilized with 70% alcohol over night, rinse 3× or gamma-irradiate, 5Gy) were then added into the tube with 5 mL of the culture medium. 10 million of the trypsinized cells per 0.3 mL of medium packed beads were then transferred into the polycarbonate tube filled with 5–6 mL medium. The tubes were then placed in tissue culture incubator on a test tube rotator that was placed titled in about 20 degrees so that the tubes rotate sidewise in about 30 rpm and the medium does not reach the punctured test tube top cover. The tubes were vortexed once every 2 days for 10 seconds to prevent beads from clumping to each other through the cells. Medium was exchanged once every 2–3 days. After the initial 2–3 days of incubation, the tube was shaken gently and the suspension aliquot was removed. The unbound cells were counted using the MTS assay (the CellTitre 96 AQueous Assay by Promega). The results with FMB in comparison with fibrinogen-coated Sepharose Beads (SB-Fib) are presented in the table below:

TABLE 1

Cell Binding to FMB or SB-Fib (% at 4 days)

| | % Cells Bound | |
|---|---|---|
| | FMB | SB-Fib |
| Normal Cells | | |
| Human fibroblasts | 94 | 71 |
| Mouse fibroblasts | 93 | 81 |
| Human keratinocyte | 0 | 0 |
| Pig aortic smooth muscle | 98 | 74 |
| Mouse mast cell | 0 | 0 |
| Transformed Cells | | |
| 3T3 mouse fibroblast | 98 | 90 |
| OV-1063 human ovarian carcinoma | 0 | 0 |
| EMT-6 mouse mammary carcinoma | 94 | 62 |
| J774.2 mouse macrophages | 0 | 0 |
| P388-S mouse leukemia | 0 | 0 |

SEM/CFM Analysis.

Figure 4:
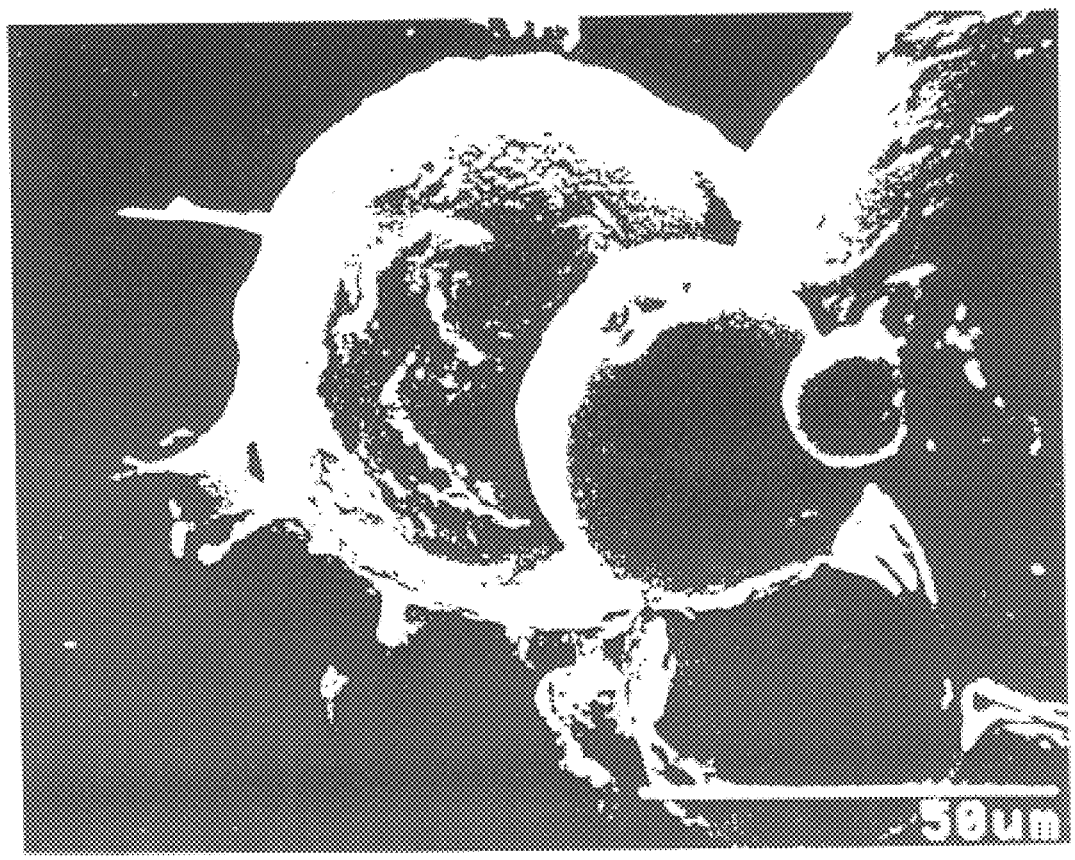
FIG. 4 represents a scanning electron micrograph of FMB of the present invention with fibroblasts, and shows how closely the cells are bound to the surface of the FMB.
Figure 5A:
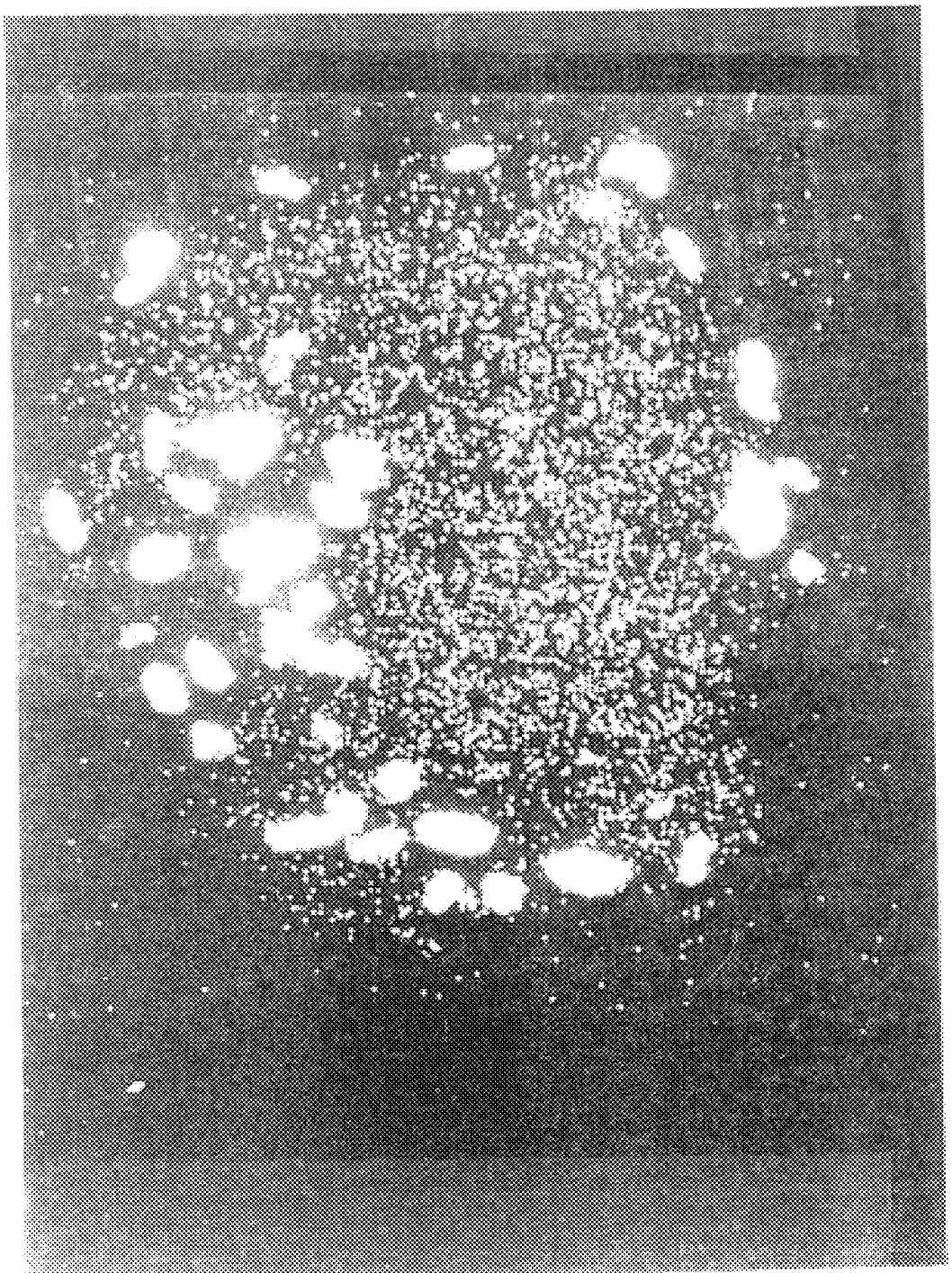
FIGS. 5A and 5B represents fluorescent micrograph of FMB of the present invention with human fibroblasts visualized by a computerized fluorescence microscope.
Figure 5B:
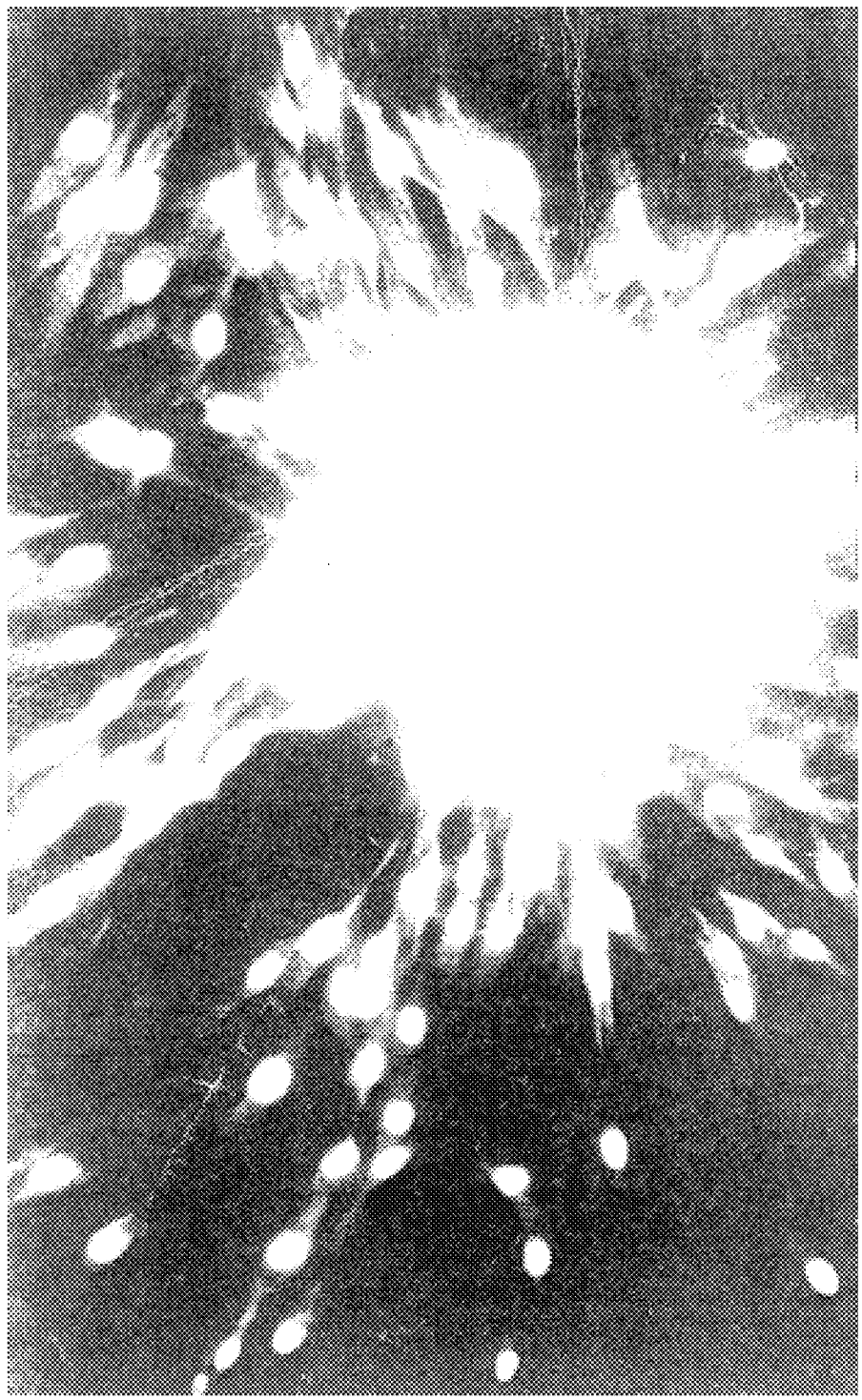

FMB with cells were prepared for scanning electron microscopy (SEM) by removing 200 μL FMB with cells from the culture medium and fixing by making up to 2% glutaraldehyde. Samples were further processed by critical point drying, coated with osmium tetroxide, sputter coated with Au/Pd and examined with a Hitachi S-530 Scanning Microscope. A scanning electron micrograph of FMB of the present invention with fibroblasts shows that the cells are bound to the surface of the FMB (see FIG. 4). A fluorescent micrograph of FMB of the present invention with human fibroblasts also was performed with a computerized confocal fluorescence microscope, and the photograph of this micrograph is shown in FIGS. 5A and 5B.

Cell Viability/Cell Density Studies.

In order to determine how long cells could remain viable on FMB, human fibroblasts on FMB were maintained in culture medium and the viability was determined by measuring viable cell density in constant volume samples of evenly distributed FMB loaded with cells using the MTS proliferation assay (the CellTitre 96 $AQ_{ueous}$ One Solution Cell Proliferation Assay by Promega). Typically, samples of 200 μl of suspended FMB+cells were placed in 24-well flat bottom plates (in triplicate) and 200 μl of freshly prepared mixture of MTS/PMC (Cell Titre 96 $AQ_{ueous}$ One Solution Cell Proliferation Assay by Promega) were added to each well, and the plate was placed on a mechanical plate incubator-shaker. After 2–6 hours of incubation at 37° C., 0.1 mL of the supernatant was transferred to a 96-well plate. The optical density (OD) of the dye was read in a computerized automatic microwell plate spectrophotometer (Anthros HT-II, Salzburg, Austria) at 490 nm. For all cell types tested, the OD readings of the MTS correlated well (r>0.97–0.99) with the number of seeded cells. It was found that FMB can be used to maintain a high cell density of viable cells for up to three weeks with initial proliferation until high density confluence of cells on beads was reached. Cell density was increased from $9.6 \times 10^5$ cells/mL to $3.6 \times 10^6$ cells per mL with 166 mg FMB.

In another experiment, EMT-6 mouse mammary carcinoma cells were loaded on FMB as follows. The cells were harvested and 3–5 million cells were added to rotating 50 mL polycarbonate tubes each with about 0.5–0.6 mL packed beads in 5–6 mL cell culture medium and rotated. Medium was exchanged on the beads every 2–3 days. After 6 days, almost total confluence of cells was recorded on the beads with cell density of about $50 \times 10^6$ cells per tube (about 0.5 mL beads).

In a further experiment, cells were loaded on FMB as follows. FMB were initially suspended in sterile alcohol for 1 hour, rinsed in sterile saline, incubated in 0.1% azide overnight at 37° C. and rinsed extensively with sterile saline. The cells to be loaded on the FMB were grown in large plastic tissue culture dishes in their normal growth conditions. Prior to reaching confluence, the cells were trypsinized, collected and added to a number of 50 mL polycarbonate tubes, each with up to 1–10 million cells per 300 mg of beads suspended in about 6 mL of medium. The tubes were covered by perforated aluminum foil and loaded on a stand that slowly rotated the tubes at about 10 cycles per minute at an angle of 30 degrees, so that the medium did not reach the perforated stoppers. The stand was placed in the $CO_2$ tissue culture incubator. A day after mixing the cells with FMB, the unattached cells were separated by brief vortexing, the tubes were kept still for 60–90 seconds to allow the FMB loaded with cells to sediment. The supernatant medium containing unattached cells as well as small fragments of FMB was removed and fresh medium added. The cells could continue growing on the FMB in the rotating device for more than 4 days.

Figure 6:
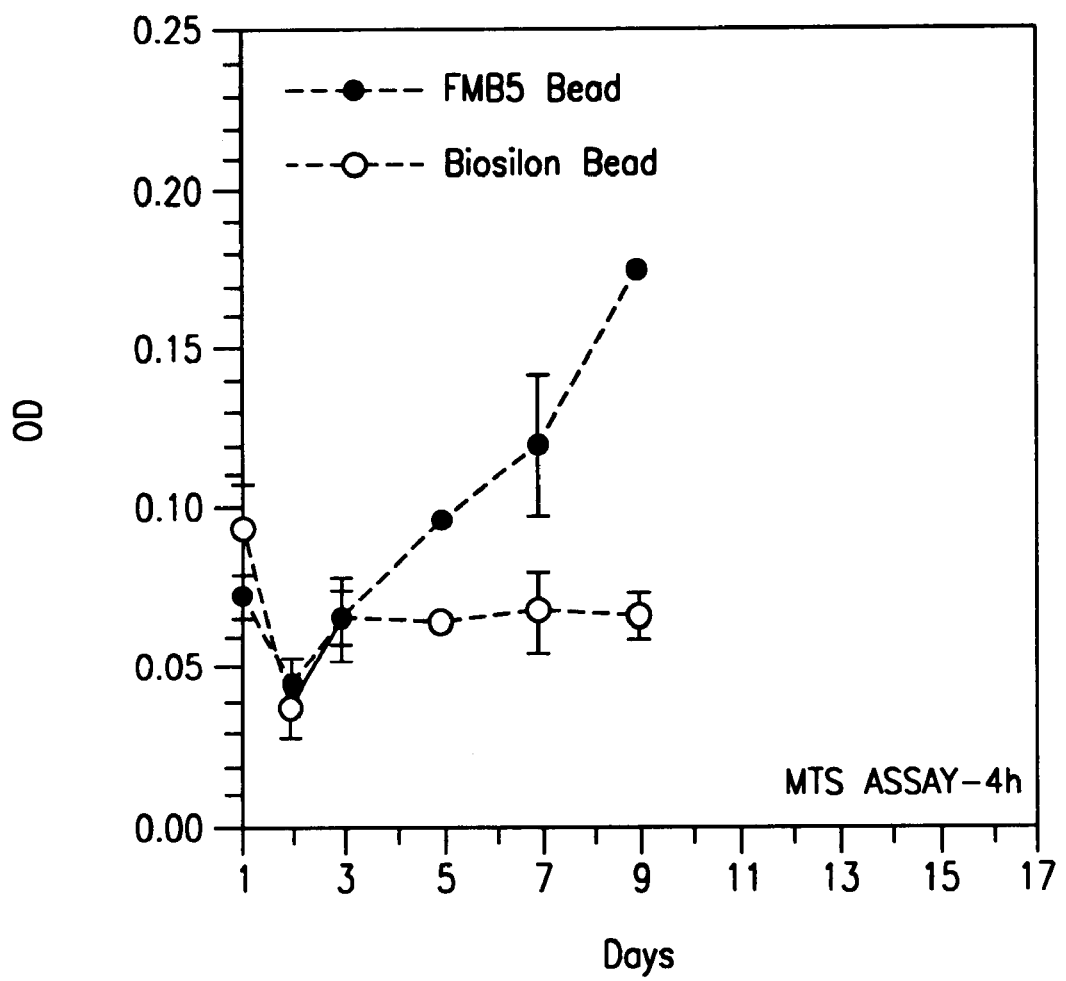
FIG. 6 represents a comparison of the growth of fibroblasts on FMB and Biosilon beads. Cell number was assayed by the MTS Assay.

In another experiment, the density of fibroblasts cultured with FMB was compared to the density of fibroblasts cultured with Biosilon micro-carrier beads (Biosilon, A/S NUNC, Foskilde, Denmark) using the MTS Assay (Berman, et al., *Biochimica et Biophysica Acta*, 1239:177–185 (1995)). In a direct comparison of fibroblasts grown on these two types of carriers, after 9 days in culture, cells on 0.37 g FMB in culture medium increased from $1.2 \times 10^5$ cells/mL to $4.8 \times 10^5$ cells (400% increase); those growing on 0.36 g Biosilon micro-carrier beads increased from $1.2 \times 10^5$ cells/mL to $1.8 \times 10^5$ cells/mL (50% increase) (see FIG. 6).

Light, Fluorescent and Confocal Laser Microscopy.

Light and fluorescent microscopy was carried out using an Olympus system at x200–x860 magnification range. Micrographs were taken by single or double (fluorescence and light) exposures. A computerized confocal lazer microscope (Zeiss Confocal Axiomate LSM410) using x63 objective with double excitation at 410 and 543 nm, was used to visualize the endogenous fluorescence of the FMB and the cell nuclei stained with propidium iodide (PI). The FMB loaded with cells were fixed in 0.5% buffered glutaraldehyde. Before examination, 50 μg/mL PI was added in darkness for at least 20 minutes. The FMB was then placed on a microscope slide with PBS-glycerol 80% and 2% DABCO, then scanned by the confocal microscope. The visual images (phase and differential interference contrast according to Nomarski) and the fluorescent slice scans were processed for overlap slice summation or 3D presentation.

$^{31}$P-NMR of Cells Loaded on FMB.

Fibroblasts, endothelial and EMT-6 cells were loaded on FMB (at about 100 million cells/g packed beads). About 1 g of FMB with cells were placed in a sterile NMR tube and perfused with the culture medium and a gas mixture of 95% $O_2$/5% $CO_2$ for up to 24 hours. As a control, fresh murine skin was cut into 2 mm wide strips, placed in the NMP tube and perfused with the medium. The 162 MHZ $^{31}$P-NMR spectra of the perfused samples were recorded on-line using Bruker AMX-400WB spectrophotometer (Sharoni, et al. *Magn. Res. Med.* 36:66–71 (1996)). Spectra were acquired using 3000 scans accumulated with 1 sec delay between the 45° pulses, spectral width of 8.5 KHz and 8000 data points. The intensity changes of the NMR resonances corresponding to inorganic phosphate ($P_i$), phospho-creatine ($P_{Cr}$) and the β-resonance of ATP were recorded.

Pig Skin Wound Healing Model.

Full thickness excisional wounds were made by an 8 mm circular punch into the paravertebral skin of Yorkshire pigs as previously described (Clark, et al. *Am. J. Pathol.* 148:1407–1421 (1996); McClain, et al. *Am. J. Pathol.* 149:1257–1270 (1996); and Welch, et al. *J. Cell Biol.* 110:133–145 (1990)). To each wound space, 150 μg of 3 mg/mL fibrinogen mixed with 2 U/mL human α-thrombin were added. In some wounds, prior to the addition of the fibrin, 0.6–1.0 million of cultured fibroblasts in suspension or on FMB were added to the bottom of the wound. Since the wounds were harvested at day 3 after the addition of fibroblasts, rejection of xeno-implanted cells was not observed. In some wounds, human platelet derived growth factor BB (PDGF-BB), a known chemotactic agent (Koyama, et al. *Circ. Res.* 75:682–691 (1994)) kindly provided by Ortho-McNeil (Princeton, N.J.) was added to the fibrinogen/thrombin solution prior to applying it to the wound. Still other wounds received all additives. Wound sites were dressed with Tegaderm, a polyurethane occlusive dressing, and harvested after 3 days. Each formulation was tested in triplicate (n=3). Specimens from all wound sites were dissected vertically. One half was fixed with formalin, paraffin embedded, sectioned at 5 μm and stained with Masson trichrome to delineate morphological alterations. The sections, which approximated the plane that vertically transected the center of each wound, were numerically coded and visually evaluated on a Nikon BHK-2 microscope by an observer who had not participated in the animal experiments.

Statistics.

The results of cell attachment and proliferation are represented in an average of 2–4 experiments. Mean values and standard errors were calculated for each point from the pooled normalized data. Statistical analysis of the significance of paired data was performed using the Student's t-test, assuming equal and unequal variance as dictated by the ANOVA test.

RESULTS

FMB Characterization.

FMB fabrication generated around 60% weight/weight yield of FMB from starting protein solutions. The FMB were not soluble in either physiologic buffers or 4N urea for up to 1 week at room temperature. This suggests significant cross-linking of the proteins. In order to evaluate this directly, 100 μg FMB were digested in 1 mL 0.1N NaOH for 1 or 2 days and the supernatant was analyzed by reduced DSD-PAGE and compared to control fibrinogen and fibrin. Densitometry of the gels showed that FMB contained many more cross-links that observed with normally clotted fibrin, which usually shows only γ—γ dimers, loss of α and γ bands as well as α—α multimers (FIGS. 3A–3C).

Attachment of FMB to Cells.

Figure 7A:
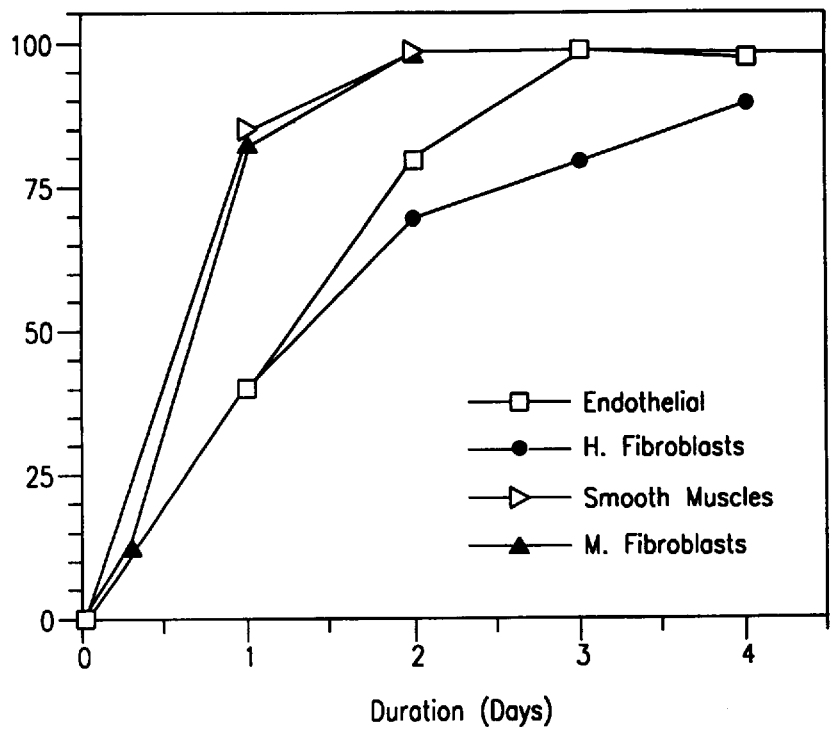
FIGS. 7A and 7B depict the responses of cells to FMB.
Figure 7B:
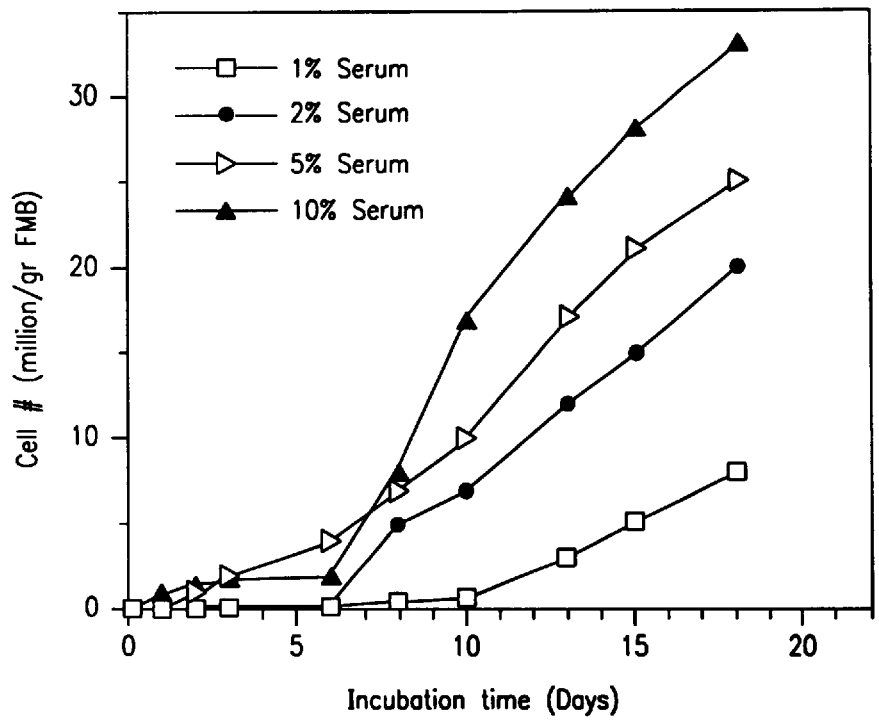

The propensity of FMB was monitored as well as Sb-Fib to be attached to the cells. Thus, either FMB or Sb-Fib were applied onto a near confluent human fibroblast culture and the proportion of beads that became attached to the cells were counted daily by phase contrast microscopy, as described (Gorodetsky, et al. *J. Lab. Clin. Med.* 131:269–280 (1998)). Control protein non-coated SB did not interact with the cells and floated freely in the culture medium even after prolonged incubation for up to a week (0% attachment). By contrast, by day 3, it was observed that the attachment kinetics of FMB to fibroblasts were similar to the response elicited by SB-Fib (FIG. 4). The attachment of FMB to other normal and transformed cells corresponded to the cell interactions with SB-Fib (FIGS. 7A and 7B, Table 2). Cells such as keratinocytes, OV-1063, and J-774.2 did not significantly attach any of the beads, whereas normal human, murine or transformed fibroblasts, smooth muscle, endothelial and EMT-6 cells attached the FMB with equal or greater degree than SB-Fib.

TABLE 2

Cell Attachment to SB-Fibrinogen and FMB (%)

| Cells | SB-Fibrinogen | FMB |
| --- | --- | --- |
| Human Fibroblasts | 70 | >95 |
| Murine Fibroblasts | 82 | >95 |
| Human Keratinocytes | 0 | 0 |
| Pig Smooth Muscle Cells | 75 | >95 |
| Bovine Endothelial Cells | >95 | >95 |
| Pig Kidney Epithelial Cells | ND | >95 |
| 3T3/NIH Fibroblasts | 90 | >95 |

TABLE 2-continued

Cell Attachment to SB-Fibrinogen and FMB (%)

| Cells | SB-Fibrinogen | FMB |
| --- | --- | --- |
| OV-1063 Human Ovarian Carcinoma Cells | 0 | 10 |
| EMT-6 Murine Mammary Carcinoma Cells | 62 | 94 |
| 4T1 Murine Mammary Carcinoma Cells | >90 | >90 |
| Human Melanoma cells | >90 | >90 |
| J-774.2 Murine Macrophage-like Cells | 0 | 0 |

Rate of Attachment of Cells to FMB.

The kinetics of hapatotactic response of fibroblasts, endothelial and smooth muscle cells to FMB (FIG. 7A) was similar to their responses to Sb-Fib (Gorodetsky, et al. *J. Lab. Clin. Med.* 131:269–280 (1998)). By day 3, most FMB were anchored to the cell layers.

Growth Kinetics on FMB.

In the interest of observing the rate of cell proliferation on FMB, the growth of pig kidney epithelial cells were monitored on FMB maintained in culture medium containing from 1% to 10% serum (FIG. 7B) with twice weekly medium replacement. The results indicate that with 10% serum, a 7-fold increase in cell number could be achieved after 1 week. By day 15, at the optimal conditions, the cells had proliferated more than 30×. Cell proliferation at lower serum concentrations was significantly lower.

The attachment and growth of cells on FMB was visualized by various microscopic techniques. By SEM, many fibroblasts could be observed attached onto a single bead with intimate contact between the cell membranes and the FMB in a manner where it was difficult to observe a boundary between the cell membrane and the surface of the microbead. (FIGS. 7A and 7B). FIG. 8A shows a confocal microscopy image of a high titer (100 million cells/g FMB) of EMT-6 cells that were loaded onto FMB for 24 hours. This image represents a composite of 50 optical slices through the FMB loaded with cells shown by their red-stained nuclei (about 8 μm in diameter). The number of cells attached to an average FMB (50–100 μm in diameter) ranged from 70 to 250 cells which typically were distributed over the whole surface and penetrated into invaginations in the FMB. When HF were grown with smaller FMB (about 30 μm in diameter) for 3 days and observed by flourescent microscopy, the cell visualized by their red-stained nuclei covered the FMB surfaces and appeared to aggregate the FMB into a tissue-like matrix with high density (FIG. 8B).

Cell Transfer With FMB.

The downloading of HF from FMB that was embedded in a droplet of fibrin (20 mg/mL) on a tissue culture plate was studied. After 3 days of incubation, the red-stained nuclei of the cells could be seen by combined fluorescent and light microscopy to expand away from the densely populated FMB into the intermediate soft fibrin gel, leaving translucent vacuoles of digested gel (FIG. 8C, around lower bead—B2). Some of the migrating cells reached the area beyond the fibrin and settled onto the less populated plastic surface. This phenomenon was also visualized with confocal fluorescent microscopy, where the PI stained nuclei revealed an expanding front of HF leaving the high cell density area on the FMB, while digesting the FMB and the surrounding fibrin gel (FIG. 8D).

$^{31}$P-Nuclear Magnetic Resonance.

Figure 9:
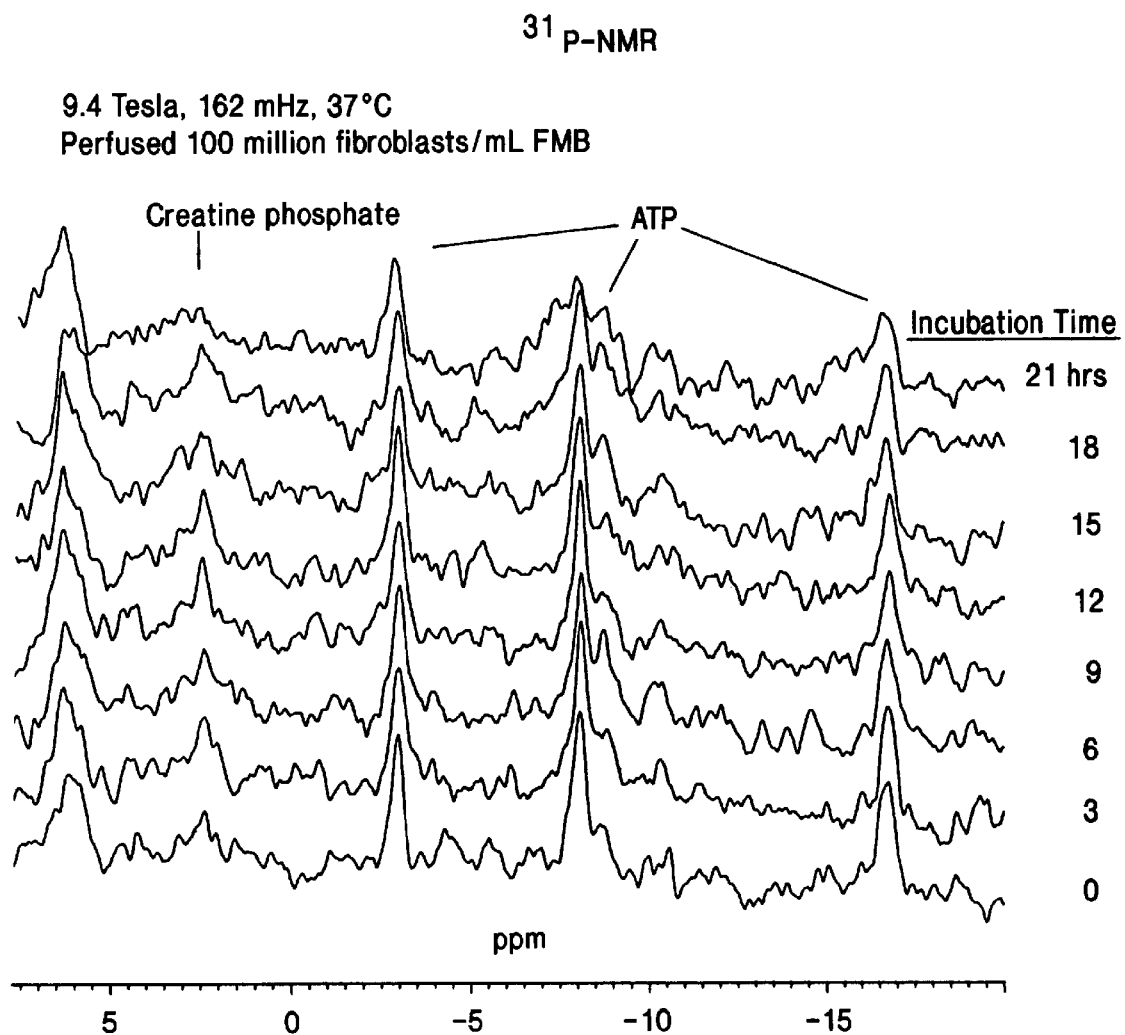
FIG. 9 sets forth a $^{31}$P-NMR spectra of endothelial cells on FMB taken over a period of up to 24 hours. The varied $P_{Cr}$ signal (~+3 ppm) indicates the stress induced consumption of the energy reserves of the cells. By contrast, the β ATP signal at ~−8 ppm reflects the cell viability with the period of the 21 hours follow-up.

Fibroblast loaded FMB, placed in a perfused NMR tube, were monitored continuously for up to 24 hours (FIG. 9). A sensitive indicator of stress is the phospho-creatine ($P_{Cr}$)

NMR signal (around 3 ppm). It gained in intensity immediately following the loading of the cells on FMB, reaching a maximum after about three hours. The intensity remained constant thereafter and declined after 18 hours. The corresponding intensity of the ATP β-phosphate resonances (−8.5 ppm) remained steady throughout the incubation period (24 hours). Similar signal intensities were recorded for perfused fresh murine skin (data not shown).

Pig Skin Wound Healing.

Figure 10A:
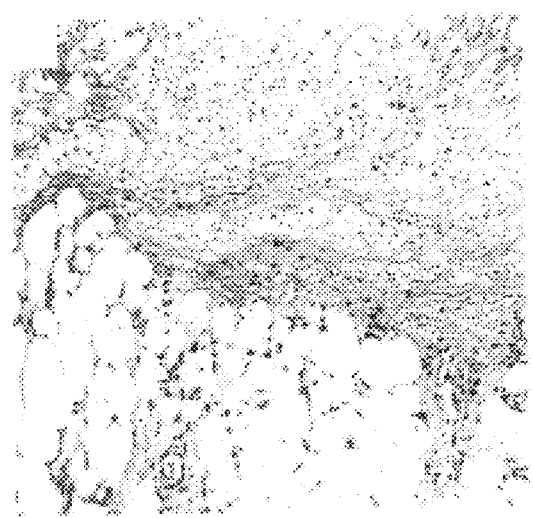
FIGS. 10A–10H represent pig skin wound healing at day 3 by the histology of porcine cutaneous wounds implanted with 3 mg/mL fibrin and combinations of FMB, human skin fibroblasts, PDGF-BB, and controls.
Figure 10B:
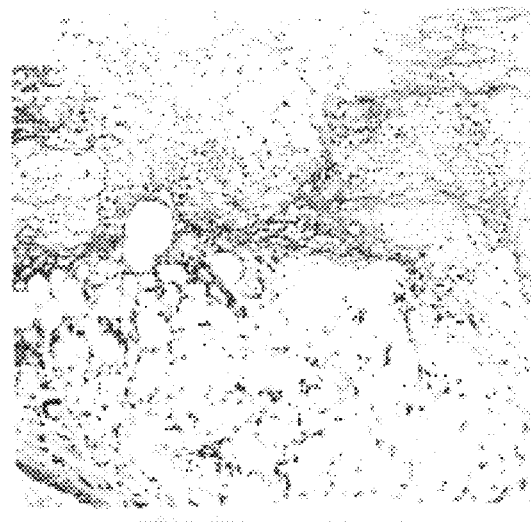
Figure 10C:
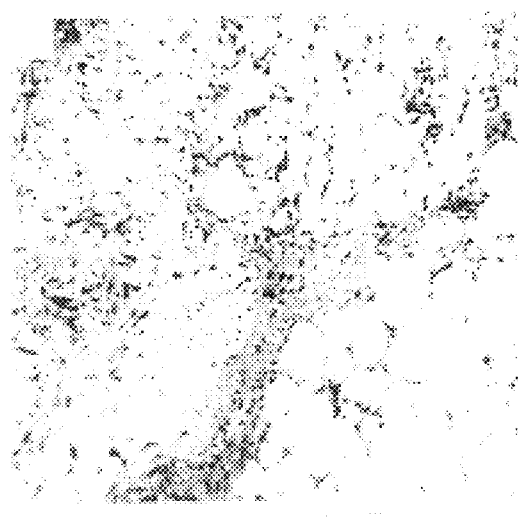
Figure 10D:
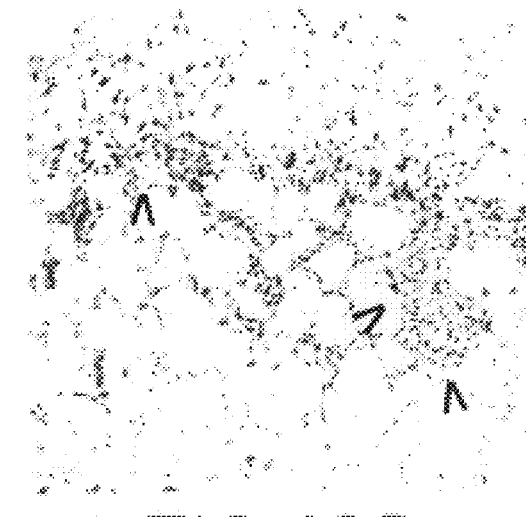
Figure 10E:
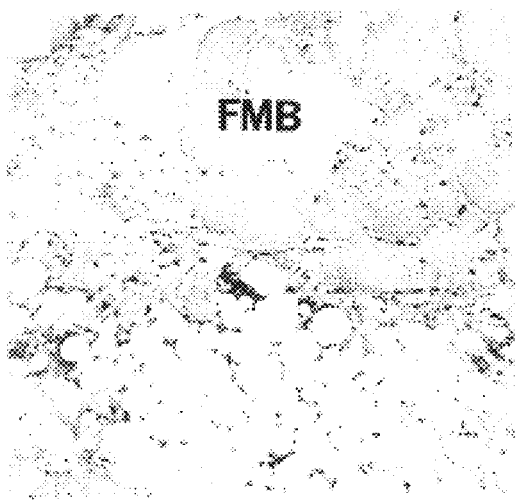
Figure 10F:
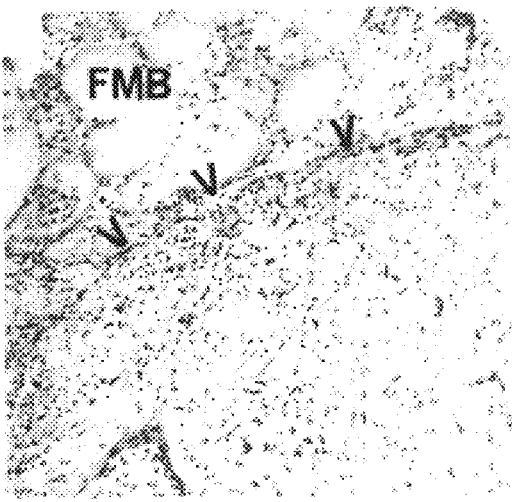
Figure 10G:
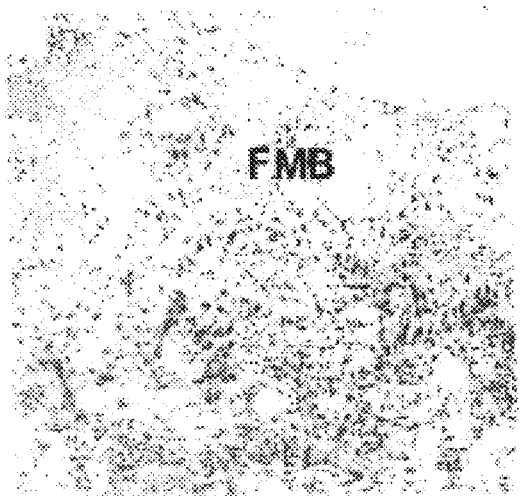
Figure 10H:
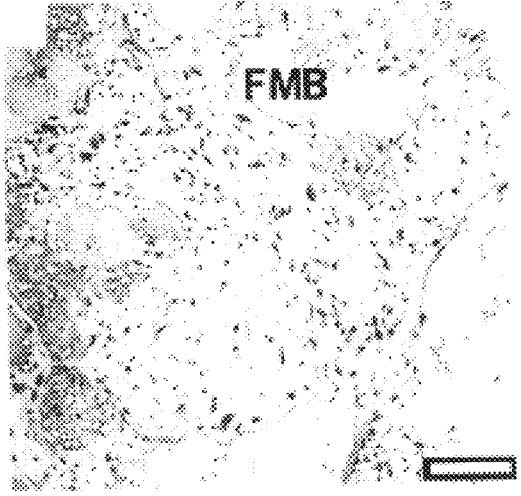

Full thickness wounds were made on the paravertebral skin of outbred Yorkshire pigs and filled with human fibrin with or without other additives or cells, as described in the Materials and Methods. All wounds were harvested at day 3, a time when granulation tissue formation normally does not occur (Clark, et al. *Am. J. Pathol.* 148:1407–1421 (1996); McClain, et al. *Am. J. Pathol.* 149:1257–1270 (1996); Welch, et al. *J. Cell Biol.* 110:133–145 (1990)). In wounds filled only with fibrin, modest fibroblast proliferation was noted in the subcutaneous tissue underlying the wounds (FIG. 10A). The number of fibroblasts increased 2–3 fold when PDGF-BB was added to the fibrin (FIG. 10B). When cultured syngeneic fibroblasts suspended in exogenous fibrin were added to the wounds, fibroblast-like cells appeared singly disposed (FIG. 10C). In wounds receiving fibroblast and PDFG-BB suspended in the fibrin, small pockets of granulation tissue were observed at the interface between the fibrin and the underlying subcutaneous tissue (FIG. 10D), as well as increased numbers of fibroblasts within the fibrin and the subcutaneous tissue. When only FMB were implanted in the wounds, they were easily visualized in the base of the wound in the newly formed granulation tissue (FIG. 6E). When PDGF-BB was included in the FMB suspension, a remarkable increase in the number of fibroblasts were noted at day 3 in the subcutaneous tissue underlying the wound (FIG. 6F). When FMB loaded with fibroblasts (10 million cells/g FMB) were applied into the wounds with fibrin, a loosely organized granulation tissue was observed at the interface between the FMB and the subcutaneous tissue (FIG. 10G). When PDGF-BB was also included, even grater amounts of more organized granulation tissue was observed (FIG. 10H). Thus, in all scenarios, FMB appeared to increase fibroblast proliferation with a significant granulation tissue formation, especially when they were used as carriers for transplanted fibroblasts. Moreover, compared to FMB control (FIG. 10E), the size of the FMB 3 days after implant was significantly smaller were significant granulation tissue was formed (FIGS. 10F–H). The biodegredation of the implanted FMB seemed to correlate with cell density of the granulation tissue.

All publications and patents mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A fibrin microbead prepared in the absence of glutaraldehyde as a cross-linking agent, wherein the fibrin microbead is prepared by a method comprising the sequential steps of: (i) preparing an aqueous solution comprising fibrinogen, thrombin and Factor XIII; (ii) prior to the onset of coagulation, contacting said aqueous solution with an oil heated to a temperature of about 50–80° C. to form an emulsion; (iii) mixing the emulsion at a temperature of about 50–80° C. until fibrin microbeads comprising extensively cross-linked fibrin(ogen) are obtained; and (iv) isolating the fibrin microbeads.

2. The fibrin microbead of claim 1, wherein at least 30% of the fibrin(ogen) is cross-linked.

3. The fibrin microbead of claim 1, wherein at least 50% of the fibrin(ogen) is cross-linked.

4. The fibrin microbead of claim 1, having a diameter of about 50–200 microns.

5. The fibrin microbead of claim 1, further comprising at least one bioactive agent.

6. The fibrin microbead of claim 5, wherein the bioactive agent is selected from the group consisting of drugs, neurologics, vitamins, vitamin derivatives, growth factors, glucocorticosteroids, steroids, antibiotics, antibacterial compounds, antiviral compounds, antifungal compounds, antiparasitic compounds, tumoricidal compounds, tumoristatic compounds, toxins, enzymes, enzyme-inhibitor proteins, peptides, minerals, neurotransmitters, lipoproteins, glycoproteins, immunomodulators, immunoglobulins, immunoglobulin fragments, dyes, radiolabels, radiopaque compounds, fluorescent compounds, fatty-acid derivatives, polysaccharides, cell-receptor-binding molecules, anti-inflammatories, antiglaucomic compounds, mydriatic compounds, anesthetics, nucleic acids, and polynucleotides.

7. A comprising cells bound to fibrin microbeads, wherein the fibrin microbeads are prepared in the absence of glutaraldehyde as a cross-linking agent, and wherein the fibrin microbeads are prepared by a method comprising the sequential steps of: (i) preparing an aqueous solution comprising fibrinogen, thrombin and Factor XIII; (ii) prior to the onset of coagulation, contacting said aqueous solution with an oil heated to a temperature of about 50–80° C. to form an emulsion; (iii) mixing the emulsion at a temperature of about 50–80° C. until fibrin microbeads comprising extensively cross-linked fibrin(ogen) are obtained; and (iv) isolating the fibrin microbeads.

8. The composition of claim 7, wherein at least 30% of the fibrin(ogen) is cross-linked.

9. The composition of claim 7, wherein at least 50% of the fibrin(ogen) is cross-linked.

10. The composition of claim 7, wherein the fibrin microbeads have a diameter of about 50–200 microns.

11. The composition of claim 7, wherein the cells are selected from the group consisting of fibroblasts, endothelial cells, chondrocytes, neuroblastoma cells, kidney cells, liver cells, pancreatic cells, thyroid cells, glial cells, smooth muscle cells, mouse mammary carcinoma cells, bone/cartilage-forming cells, and combinations thereof.

12. The composition of claim 7, wherein the fibrin microbeads further comprise at least one bioactive agent.

13. The composition of claim 12, wherein the bioactive agent is selected from the group consisting of drugs, neurologics, vitamins, vitamin derivatives, growth factors, glucocorticosteroids, steroids, antibiotics, antibacterial compounds, antiviral compounds, antifungal compounds, antiparasitic compounds, tumoricidal compounds, tumoristatic compounds, toxins, enzymes, enzyme-inhibitor proteins, peptides, minerals, neurotransmitters, lipoproteins, glycoproteins, immunomodulators, immunoglobulins, immunoglobulin fragments, dyes, radiolabels, radiopaque compounds, fluorescent compounds, fatty-acid derivatives, polysaccharides, cell-receptor-binding molecules, anti-inflammatories, antiglaucomic compounds, mydriatic compounds, anesthetics, nucleic acids, and polynucleotides.

14. The composition of claim 7, wherein the cells are infected with a virus.

15. The composition of claim 7, wherein the cells express a recombinant protein.

16. The composition of claim 7, wherein the cells contain exogenous nucleic acid.

17. A method for culturing cells, comprising the step of culturing fibrin-microbead-binding cells with fibrin microbeads in a culture medium, under conditions permitting the cells to bind to the fibrin microbeads, wherein the fibrin microbeads are prepared in the absence of glutaraldehyde as a cross-linking agent, and wherein the fibrin microbeads are prepared by a method comprising the sequential steps of: (i) preparing an aqueous solution comprising fibrinogen, thrombin and Factor XIII; (ii) prior to the onset of coagulation, contacting said aqueous solution with an oil heated to a temperature of about 50–80° C. to form an emulsion; (iii) mixing the emulsion at a temperature of about 50–80° C. until fibrin microbeads comprising extensively cross-linked fibrin(ogen) are obtained; and (iv) isolating the fibrin microbeads.

18. The method of claim 17, wherein at least 30% of the fibrin(ogen) is cross-linked.

19. The method of claim 17, wherein at least 50% of the fibrin(ogen) is cross-linked.

20. The method of claim 17, wherein the fibrin microbeads have a diameter of about 50–200 microns.

21. The method of claim 17, wherein the fibrin-microbead-binding cells are selected from the group consisting of fibroblasts, endothelial cells, chondrocytes, neuroblastoma cells, kidney cells, liver cells, pancreatic cells, thyroid cells, glial cells, smooth muscle cells, mouse mammary carcinoma cells, bone/cartilage-forming cells, and combinations thereof.

22. The method of claim 17, further comprising the step of isolating the fibrin microbeads from the culture medium.

23. The method of claim 17, wherein the fibrin microbeads further comprise at least one bioactive agent.

24. The method of claim 23, wherein the bioactive agent is selected from the group consisting of drugs, neurologics, vitamins, vitamin derivatives, growth factors, glucocorticosteroids, steroids, antibiotics, antibacterial compounds, antiviral compounds, antifungal compounds, antiparasitic compounds, tumoricidal compounds, tumoristatic compounds, toxins, enzymes, enzyme-inhibitor proteins, peptides, minerals, neurotransmitters, lipoproteins, glycoproteins, immunomodulators, immunoglobulins, immunoglobulin fragments, dyes, radiolabels, radiopaque compounds, fluorescent compounds, fatty-acid derivatives, polysaccharides, cell-receptor-binding molecules, anti-inflammatories, antiglaucomic compounds, mydriatic compounds, anesthetics, nucleic acids, and polynucleotides.

25. The method of claim 17, wherein the cells are infected with a virus.

26. The method of claim 25, further comprising the step of isolating the virus from the cell culture.

27. The method of claim 17, wherein the cells produce a recombinant protein.

28. The method of claim 27, further comprising the step of isolating the recombinant protein from the cell culture.

29. The method of claim 17, wherein the cells contain exogenous nucleic acid.

30. The method of claim 29, further comprising the step of isolating the exogenous nucleic acid from the cell culture.

* * * * *

UNITED STATES PATENT AND TRADEMARK OFFICE
CERTIFICATE OF CORRECTION

PATENT NO.    : 6,503,731 B2
DATED         : January 7, 2003
INVENTOR(S)   : Gerald Marx and Raphael Gorodetsky It is certified that error appears in the above-identified patent and that said Letters Patent is hereby corrected as shown below:

Column 16,
Line 24, "7. A comprising cells bound to fibrin microbeads, wherein" should read
-- 7. A composition comprising cells bound to fibrin microbeads, wherein --

Signed and Sealed this

Thirty-first Day of August, 2004

JON W. DUDAS
*Director of the United States Patent and Trademark Office*